US006783551B1

(12) United States Patent
Metzger et al.

(10) Patent No.: US 6,783,551 B1
(45) Date of Patent: *Aug. 31, 2004

(54) METHOD AND APPARATUS FOR ENABLING ACCESS TO AN INTRAMEDULLARY CANAL OF A FEMUR THROUGH A FEMORAL KNEE JOINT PROSTHESIS

(75) Inventors: Robert Metzger, Walkarusa, IN (US); Jacy Charles Hoeppner, Syracuse, IN (US); David Ray Brown, Warsaw, IN (US); Gregory David VanDeWater, Warsaw, IN (US)

(73) Assignee: Biomet, Inc., Warsaw, IN (US)

( * ) Notice: Subject to any disclaimer, the term of this patent is extended or adjusted under 35 U.S.C. 154(b) by 2 days.

This patent is subject to a terminal disclaimer.

(21) Appl. No.: 10/134,739

(22) Filed: Apr. 29, 2002

Related U.S. Application Data

(63) Continuation-in-part of application No. 09/738,111, filed on Dec. 15, 2000, now Pat. No. 6,416,552, which is a continuation-in-part of application No. 09/223,616, filed on Dec. 30, 1998, now Pat. No. 6,165,222.

(51) Int. Cl.[7] .................................................. A61F 2/38
(52) U.S. Cl. .................................................. 623/20.31
(58) Field of Search ........................... 623/20.14, 20.15, 623/20.31, 20.36, 22.34, 23.2, 23.28

(56) References Cited

U.S. PATENT DOCUMENTS

| | | | |
|---|---|---|---|
| 5,009,666 A | * 4/1991 | Van Syckle et al. | ...... 623/23.28 |
| 5,019,108 A | * 5/1991 | Bertin et al. | ............. 623/23.28 |
| 5,147,406 A | 9/1992 | Houston et al. | |
| 5,152,796 A | 10/1992 | Slamin | |
| 5,181,925 A | 1/1993 | Houston et al. | |
| 5,192,331 A | * 3/1993 | Spotorno et al. | ........ 623/23.28 |
| 5,326,359 A | 7/1994 | Oudard | |
| 5,330,534 A | 7/1994 | Herrington et al. | |

5,370,702 A * 12/1994 Jones ....................... 623/22.34

(List continued on next page.)

FOREIGN PATENT DOCUMENTS

WO WO00/38598 7/2000

OTHER PUBLICATIONS

US 5,387,242, 2/1995, Miser (withdrawn)
Biomet, Inc., "AGC Total Knee System, Tradition Series", copyright 1995.
Biomet, Inc., "Performance The Total Knee System," copyright 1997.
Biomet, Inc., "Maxim The Complete Knee System," copyright 1995.
Biomet, Inc., Medical Products, "Biomet Retrograde Femoral Nail," copyright 1995.
Biomet, Inc., "Biomet Retrograde Femoral Nail Surgical Technique", copyright 1995.
Richards, "Genesis Total Knee System Bone Augmentation: Stems and Wedges".
The Journal of Bone and Joint Surgery, Aug. 1997, 79–A.

*Primary Examiner*—David J. Isabella
(74) *Attorney, Agent, or Firm*—Harness, Dickey & Pierce, P.L.C.

(57) ABSTRACT

A method and apparatus for enabling access to an intramedullary canal of a femur through a femoral knee joint prosthesis includes a first condylar portion and a second condylar portion. The first condylar portion has a first femoral bearing surface and the second condylar portion has a second femoral bearing surface. An inner condylar portion extends between the first condylar portion and the second condylar portion and defines an opening passing therethrough. A seal member is operable to substantially seal the opening such that the seal member is further operable to be opened to enable access to the intramedullary canal of the femur without having to remove the femoral knee joint prosthesis from the femur. A method for enabling access to the intramedullary canal of the femur through the femoral knee joint prosthesis is also provided.

21 Claims, 16 Drawing Sheets

U.S. PATENT DOCUMENTS

| | | |
|---|---|---|
| 5,405,349 A | 4/1995 | Burkinshaw et al. |
| 5,405,395 A | 4/1995 | Coates |
| 5,405,398 A | 4/1995 | Buford, III et al. |
| 5,554,158 A | 9/1996 | Vinciguerra et al. |
| 5,556,433 A | 9/1996 | Gabriel et al. |
| 5,593,449 A | 1/1997 | Roberson, Jr. |
| 5,645,606 A * | 7/1997 | Oehy et al. ............... 623/22.34 |
| 5,681,353 A | 10/1997 | Li et al. |
| 5,683,472 A | 11/1997 | O'Neil et al. |
| 5,782,929 A * | 7/1998 | Sederholm ............... 623/22.34 |
| 5,879,391 A | 3/1999 | Slamin |
| 6,152,962 A * | 11/2000 | DeCarlo, Jr. ............. 623/22.34 |
| 6,165,222 A | 12/2000 | Hoeppner et al. |
| 6,416,552 B1 * | 7/2002 | Hoeppner et al. ....... 623/20.15 |

\* cited by examiner

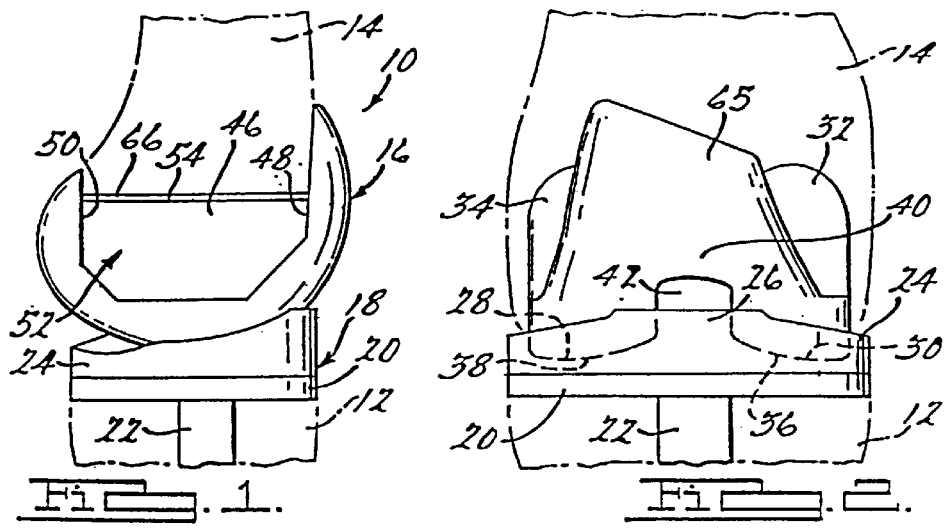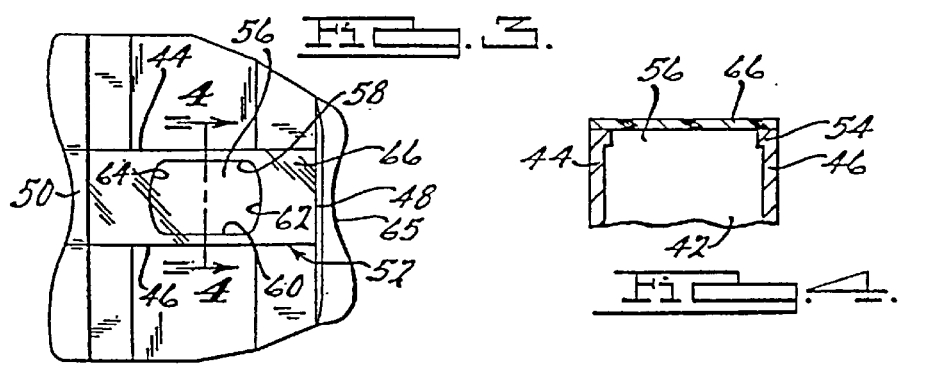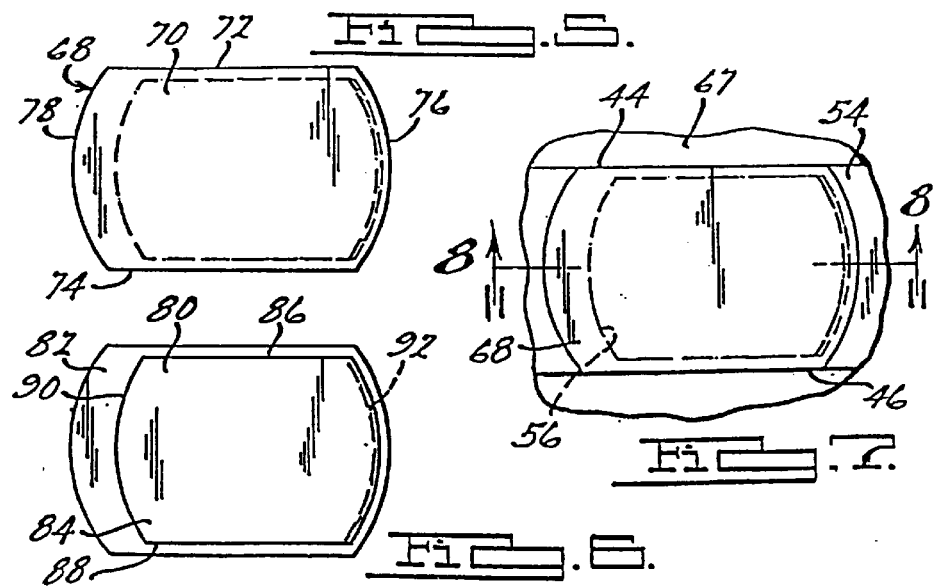

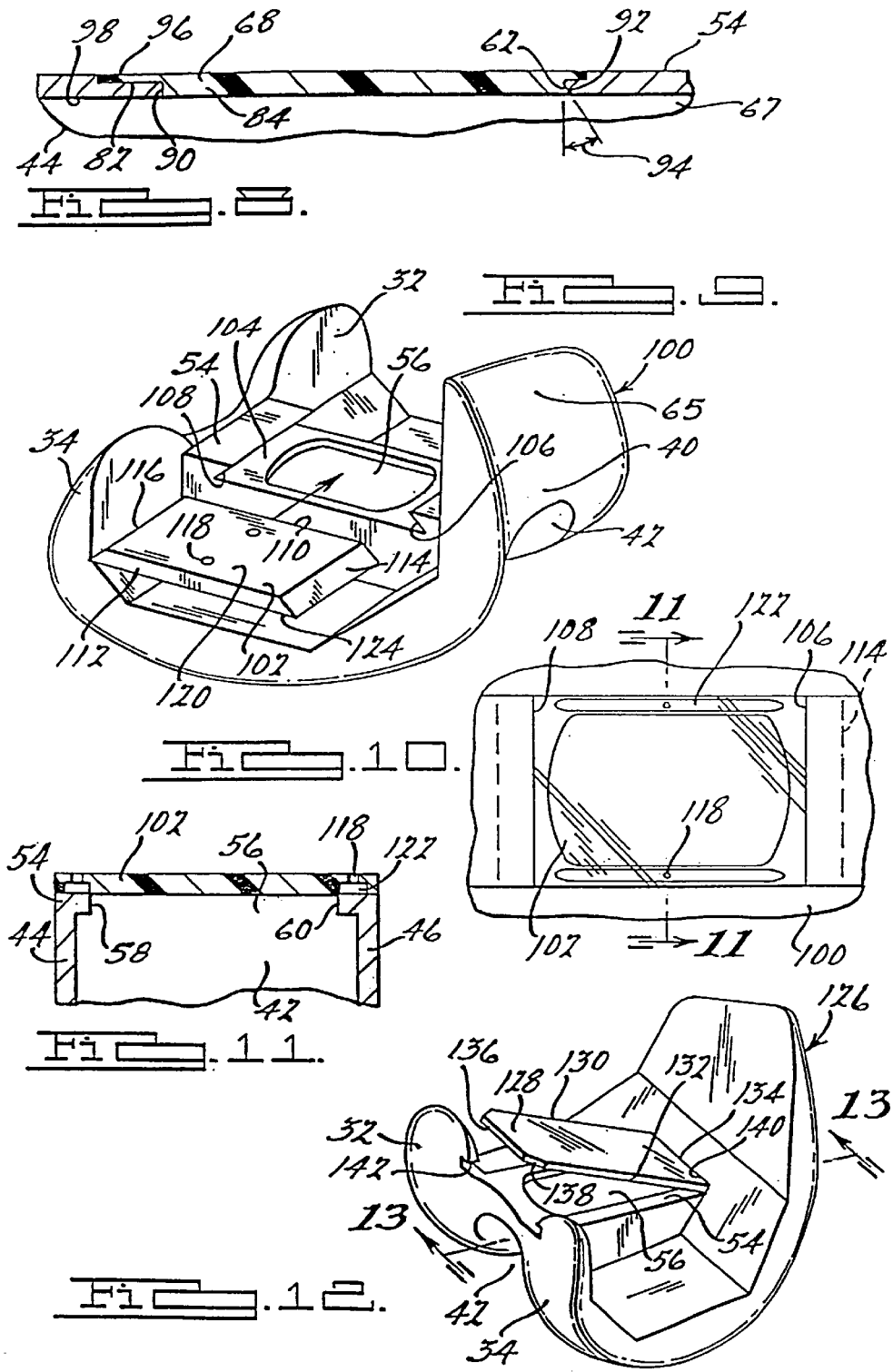

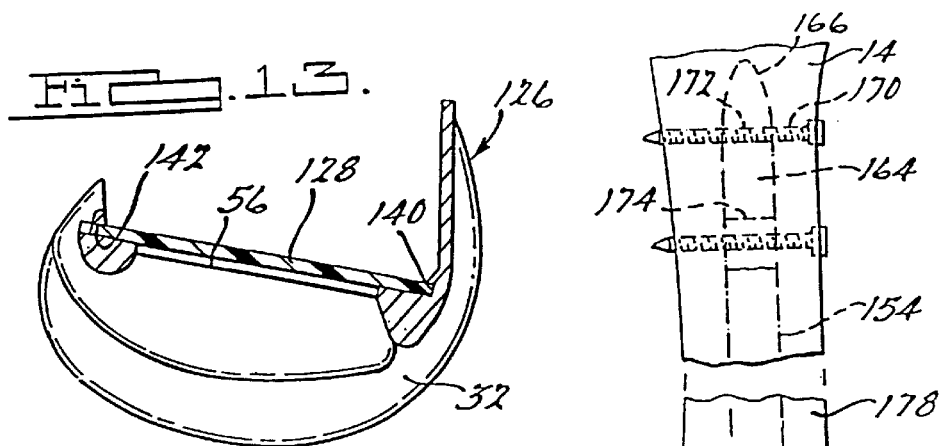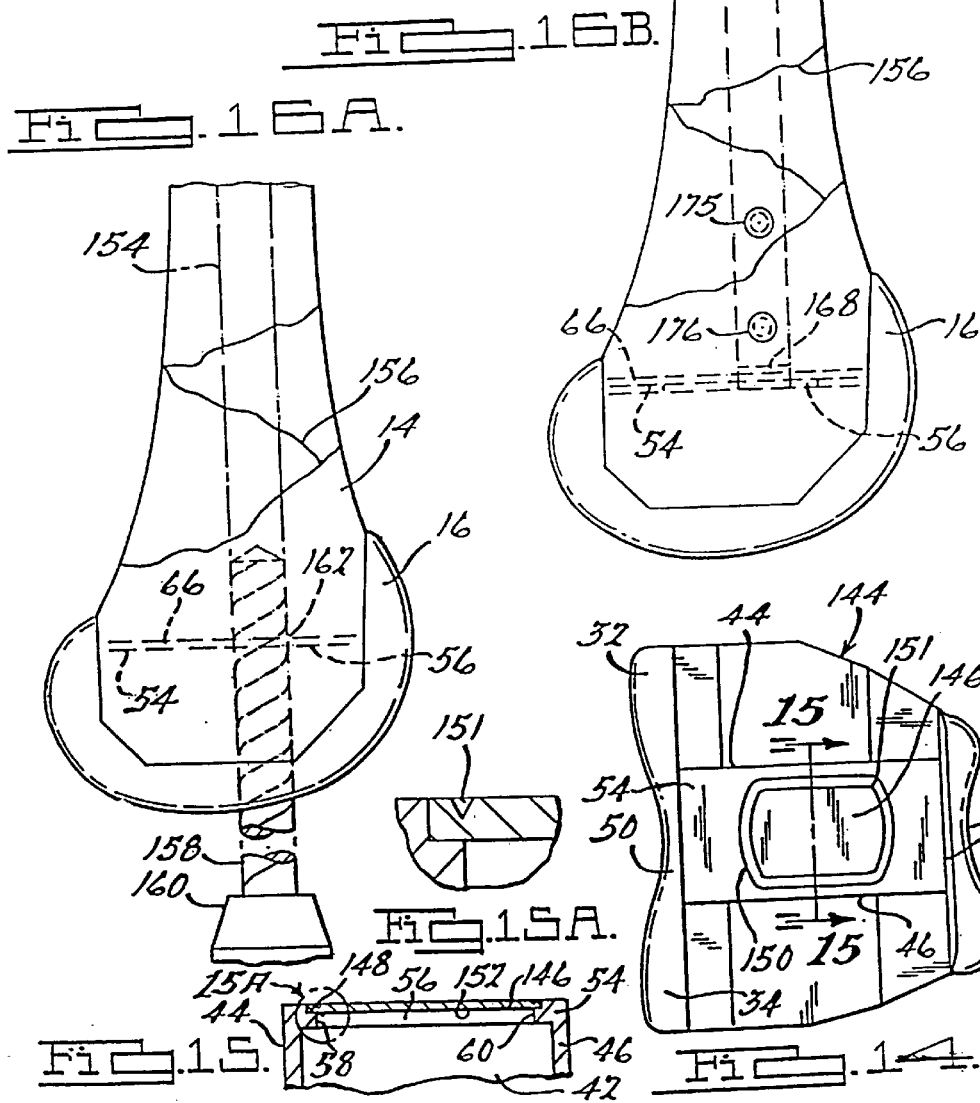

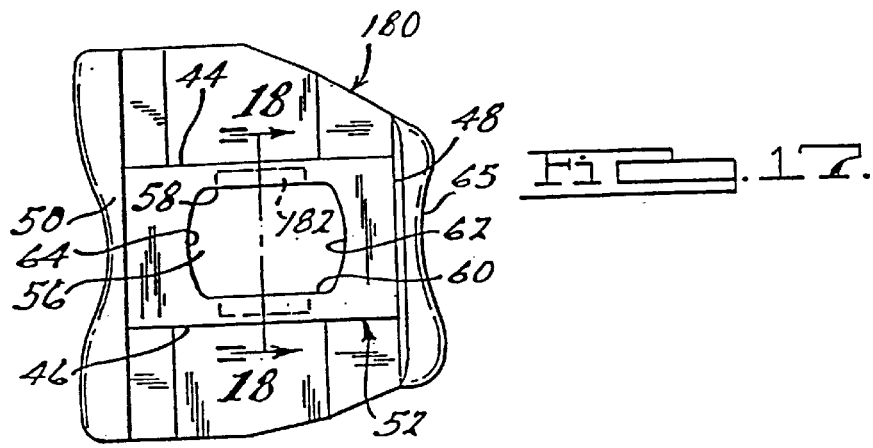
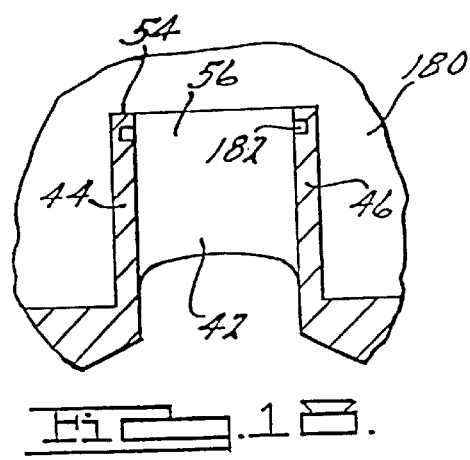
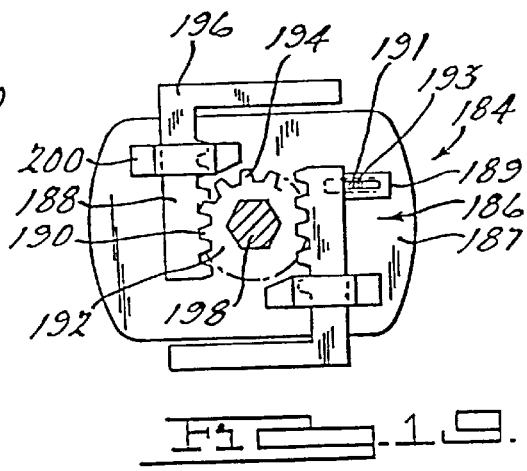

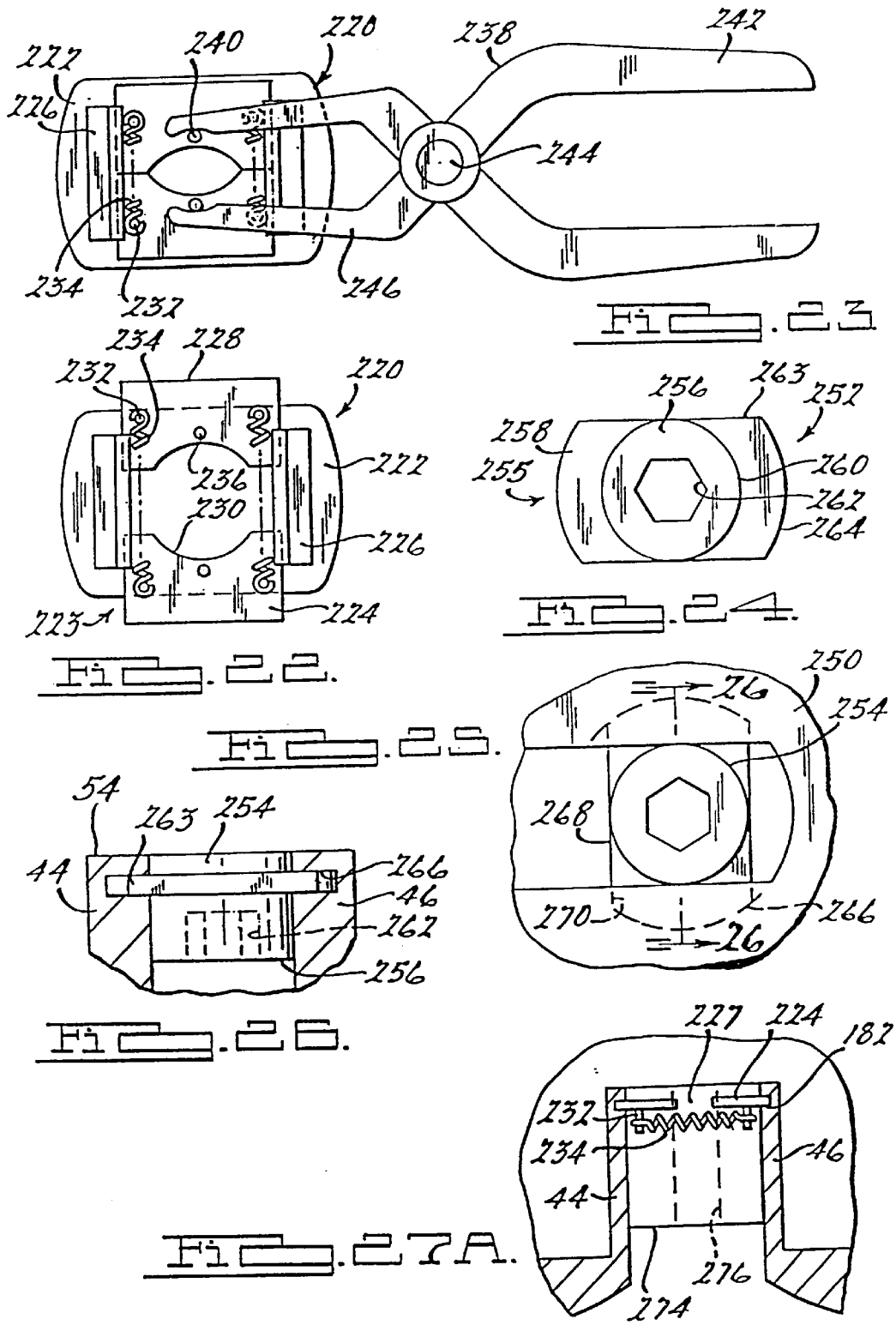

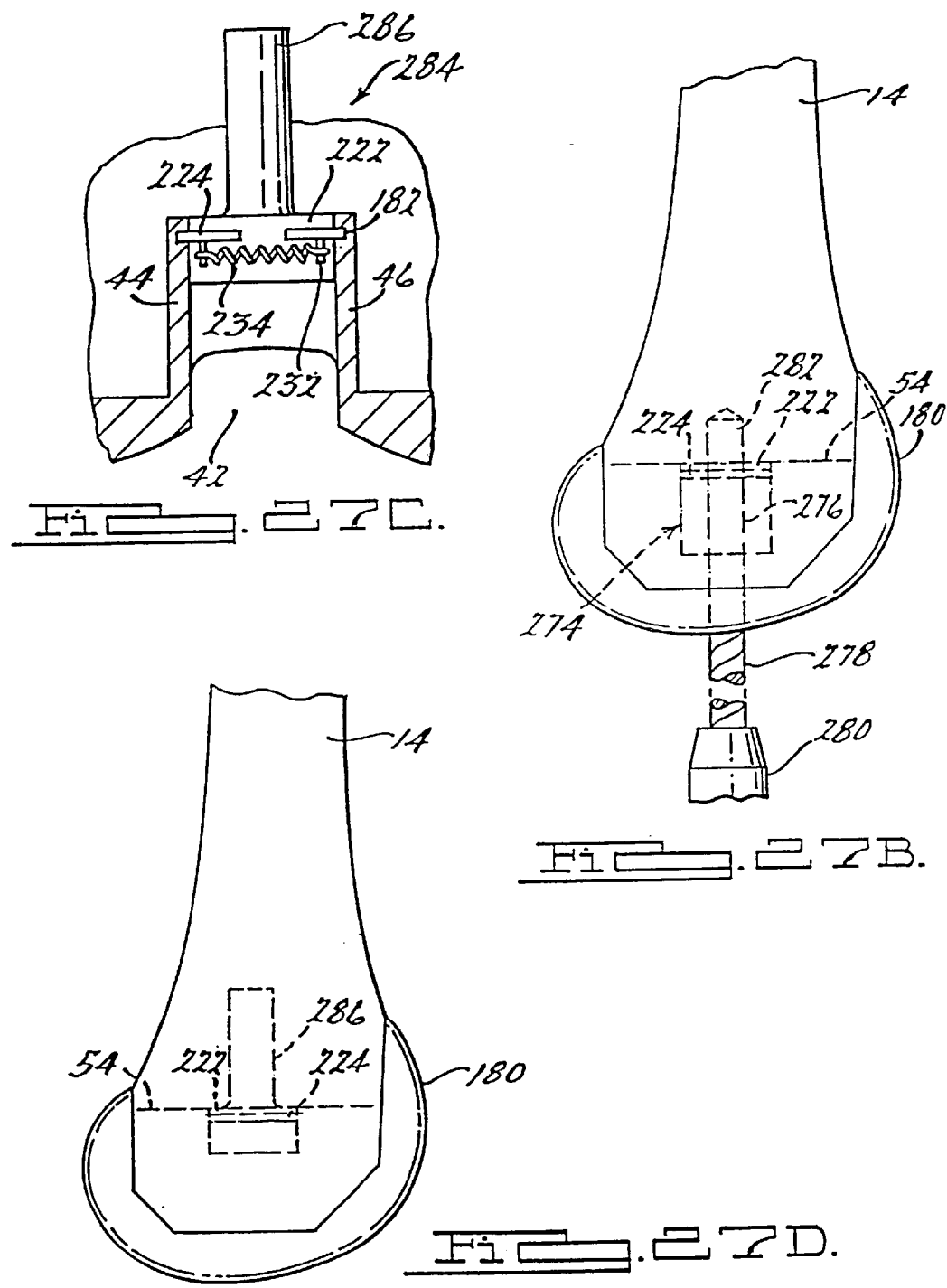

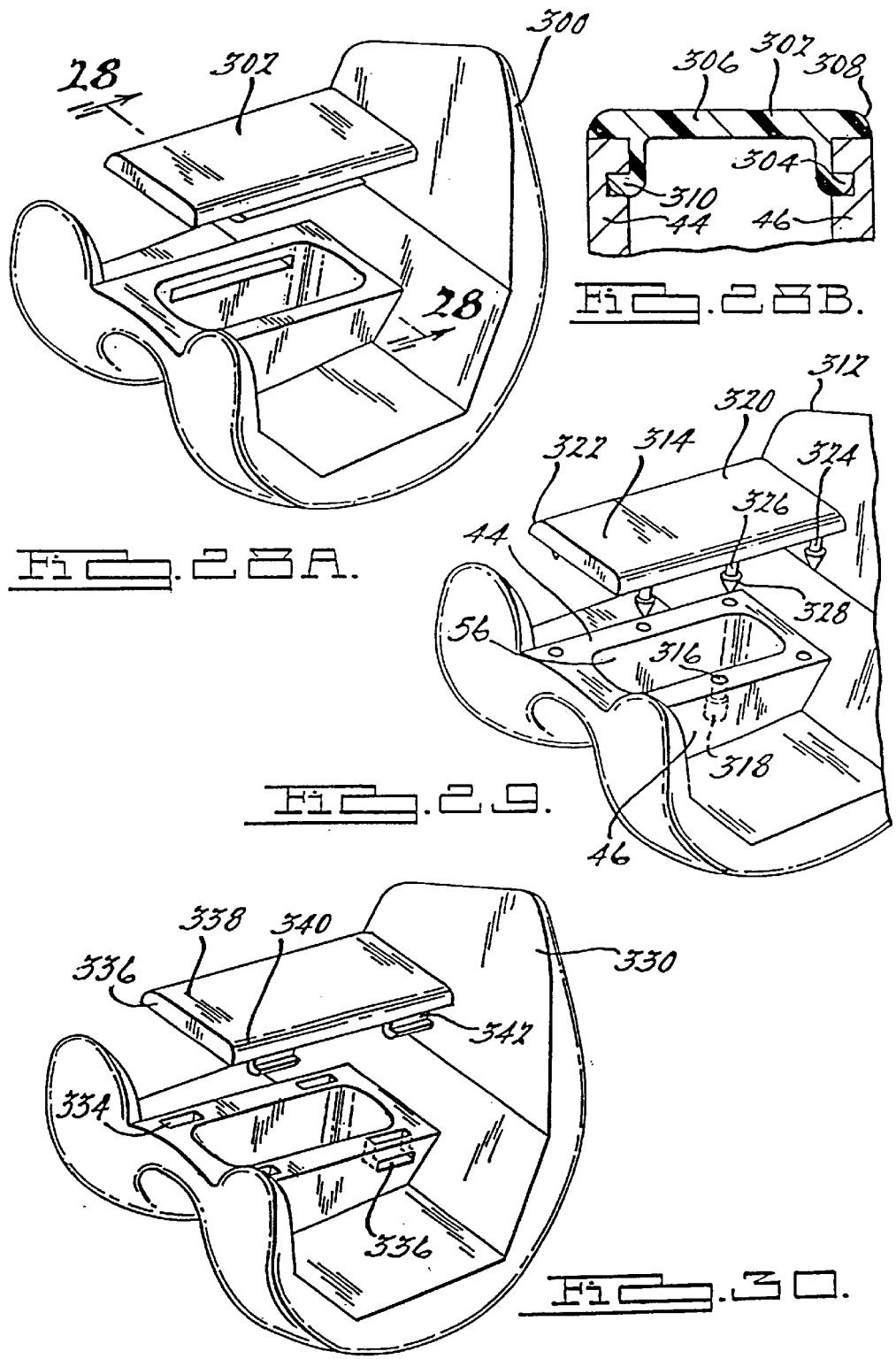

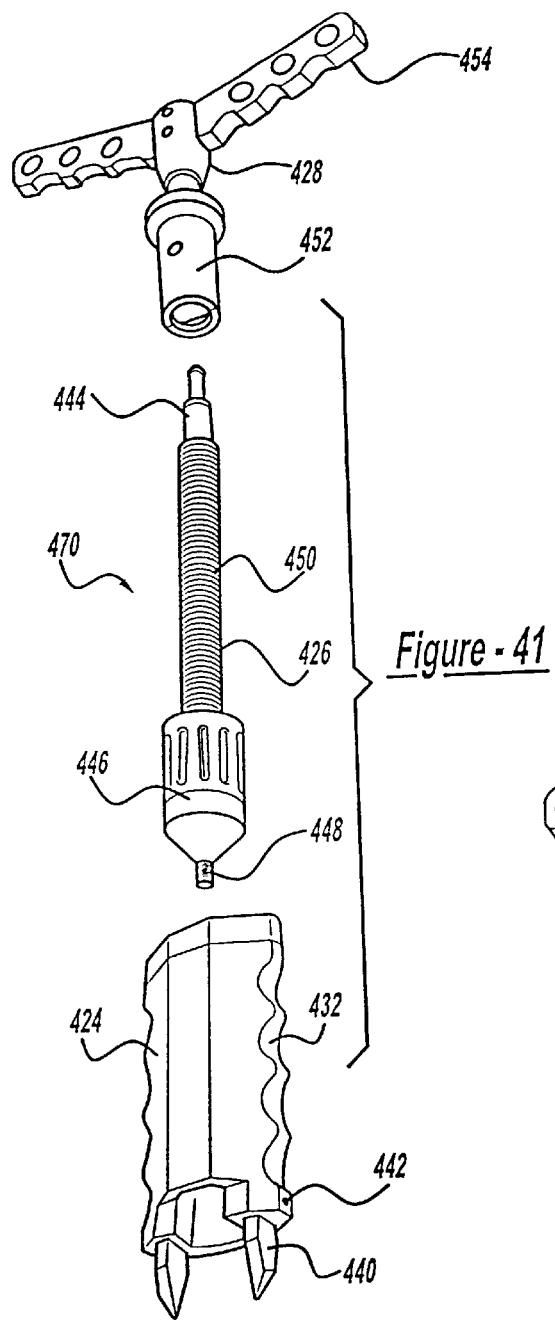
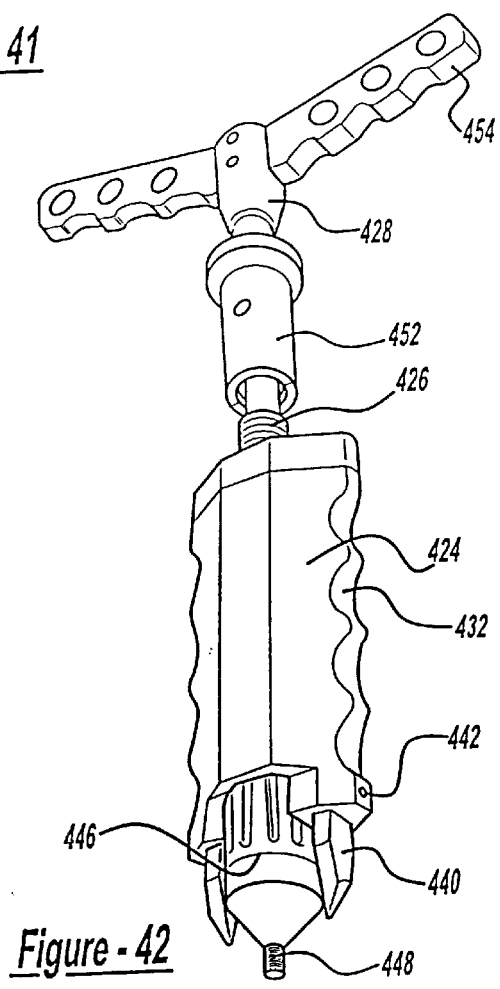
Figure - 41
Figure - 42

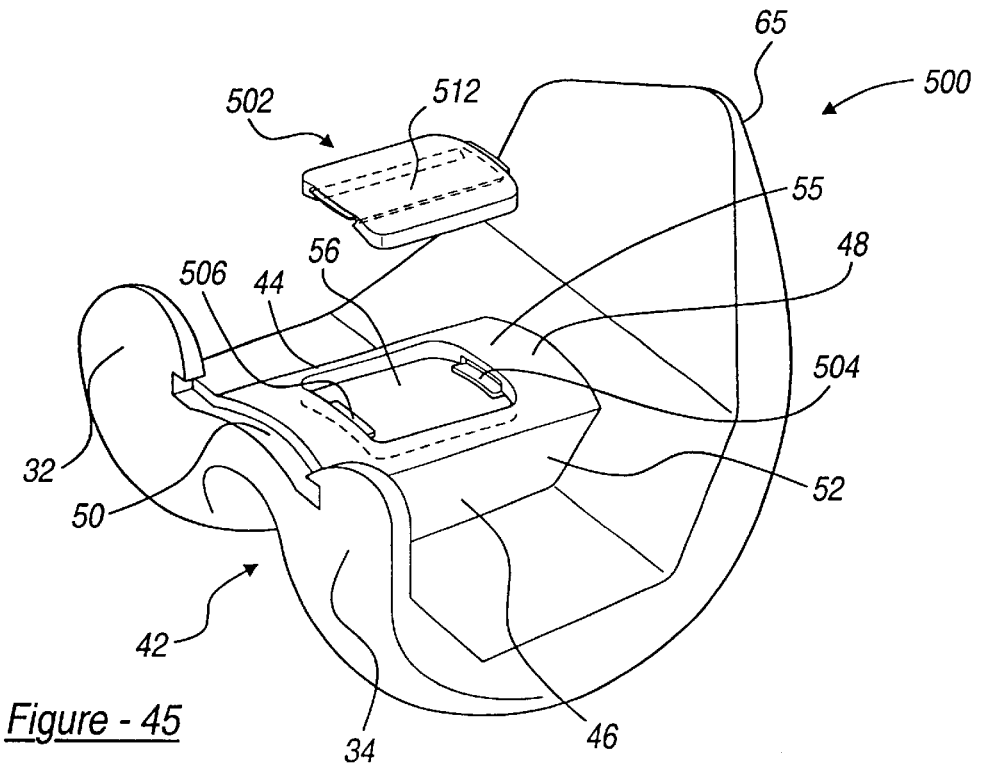
Figure - 45
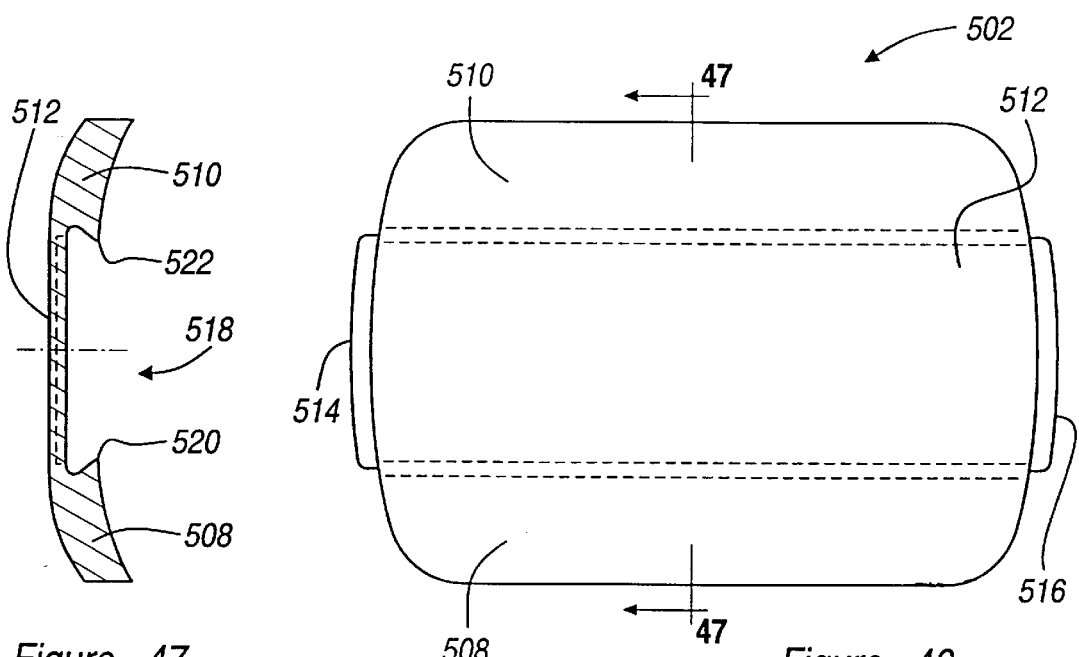
Figure - 47
Figure - 46

METHOD AND APPARATUS FOR ENABLING ACCESS TO AN INTRAMEDULLARY CANAL OF A FEMUR THROUGH A FEMORAL KNEE JOINT PROSTHESIS

CROSS REFERENCE TO RELATED APPLICATION

This is a continuation-in-part application of U.S. Ser. No. 09/738,111, filed Dec. 15, 2000 now U.S. Pat. No. 6,416,552, entitled, "Method and Apparatus For Enabling Access To An Intramedullary Canal of a Femur Through a Femoral Knee Joint Prosthesis," now allowed, but co-pending; which is a continuation-in-part of U.S. Ser. No. 09/223,616 filed Dec. 30, 1998, entitled, "Method and Apparatus For Enabling Access To An Intramedullary Canal of a Femur Through a Femoral Knee Joint Prosthesis," now U.S. Pat. No. 6,165,222. The disclosures of the above applications are incorporated herein by reference.

FIELD OF THE INVENTION

The present invention relates generally to a method and apparatus for use in orthopedic surgical procedures, and more particularly to a method and apparatus for enabling access to an intramedullary canal of a femur through a femoral knee joint prosthesis.

BACKGROUND OF THE INVENTION

A knee joint prosthesis typically comprises a femoral component and a tibial component. The femoral component and the tibial component are designed to be surgically attached to the distal end of the femur and the proximal end of the tibia, respectively. The femoral component is further designed to cooperate with the tibial component in simulating the articulating motion of an anatomical knee joint.

Motion of a natural knee is kinematically complex. During a relatively broad range of flexion and extension, the articular surfaces of a natural knee experiences rotation, medial and lateral angulation, translation in the sagittal plane, rollback and sliding. Knee joint prostheses, in combination with the ligaments and muscles, attempt to allow natural knee motion, as well as absorb and control forces generated during the range of flexion. Depending on the degree of damage or deterioration of the knee tendons and ligaments, it may also be necessary for a knee joint prosthesis to limit one or more of these motions in order to provide adequate stability.

After the knee joint prosthesis is implanted into a patient, there may be situations which require access to the intramedullary canal of the femur, proximal to the femoral component. For example, should a supracondylar fracture occur above the anterior flange of the femur, this fracture may require a femoral nail to provide patient stability. Use of currently available posterior stabilized (PS) femoral components, however, pose various advantages and disadvantages when access to the intramedullary canal is required.

PS femoral components having a "closed box" provide the advantage of preventing debris migration into the articulating joint area, as well as preventing bone cement from passing through the opening to interfere with the tibial component. However, because the top of the box is closed, one way to insert a femoral nail involves removing the PS femoral component, implanting the femoral nail, and reimplanting a new revision PS femoral component. Alternatively, a high speed burr may be used to create a hole through the solid box, thereby creating sharp metal debris that may easily damage the rest of the femoral component.

Should an "open box" PS femoral component be utilized, a femoral nail may be passed through the top of the box and into the intramedullary canal without the disadvantages of the closed box. However, an "open box" PS femoral component also allows increased debris, bone chips or bone cement to pass through into the articulating joint area both during implantation and during use. As such, the use of "open box" or "closed box" PS femoral components each exhibit different advantages and disadvantages.

Another method for assisting in the healing of a supracondylar fracture or to improve patient instability is to modify the knee joint prosthesis with a constrained femoral component. This is generally achieved by providing a femoral component with an intramedullary stem that extends from the box. Here again, with existing stemmed femoral components, the stem is either integral with the femoral component or it must be attached to a modular femoral component before the component is implanted. In such cases, modular knee joint prosthetic devices are available which enables different boxes or different length stems to be coupled to the femoral component. However, these modular knee joint prosthetic devices require assembly before the prosthetic device is implanted and do not allow later intraoperative modification of the knee joint prosthesis without removal of the femoral component itself. This would, therefore, again require the femoral component to be removed with a new revision femoral component being subsequently implanted that has the intramedullary stem.

What is needed then is a method and apparatus for enabling access to an intramedullary canal of a femur through the femoral component of the knee joint prosthesis which does not suffer from the above mentioned disadvantages. This, in turn, will eliminate the need for removal of the femoral component to insert a femoral nail or a femoral stem; provide a closed box which has the advantage of preventing debris or bone cement from entering the articulating joint area; provide an easy mechanism to open the top of the box intraoperatively when it is desired to gain access to the intramedullary canal of the femur without having to remove the femoral component; reduce overall surgical cost, time and complexity to correct a supracondylar fracture; and provide a convertible sealed top which may be subsequently opened after the knee joint prosthesis has been implanted to provide the benefits of both a "closed box" femoral component and an "open box" femoral component. It is, therefore, an object of the present invention to provide such a method and apparatus for enabling access to an intramedullary canal of a femur through a femoral knee joint prosthesis.

SUMMARY OF THE INVENTION

In accordance with the teachings of the present invention, a method and apparatus for enabling access to an intramedullary canal of a femur through a femoral knee joint prosthesis is disclosed. This is basically achieved by providing a femoral knee joint prosthesis that defines a bore passing therethrough. A seal member seals the bore and is operable to be opened to enable access to the intramedullary canal of the femur.

In one preferred embodiment, a femoral knee joint prosthesis for allowing access to an intramedullary canal of a femur after the femoral knee joint prosthesis has been implanted includes a first condylar portion and a second condylar portion. The first condylar portion has a first femoral bearing surface and the second condylar portion has a second femoral bearing surface. An inner condylar portion extends between the first condylar portion and the second condylar portion and defines an opening passing therethrough. A seal member is operable to seal the opening in the top such that the seal member is further operable to be opened to enable access to the intramedullary canal of the femur without having to remove the femoral knee joint prosthesis from the femur.

In another preferred embodiment, a knee joint prosthesis for enabling access to an intramedullary canal of a femur includes a femoral component having at least one bearing surface and defining a bore passing therethrough. A tibial component having a second bearing surface is operable to articulate with the first bearing surface of the femoral component. A seal member is operable to seal the bore in the femoral component such that the seal member may be opened after the femoral component is implanted to enable access to the intramedullary canal of the femur.

In another preferred embodiment, a method for enabling access to an intramedullary canal of a femur through a femoral knee joint prosthesis includes implanting the femoral knee joint prosthesis having a seal member which seals a bore passing through the femoral knee joint prosthesis. Thereafter, the seal member in the femoral knee joint prosthesis is opened after the femoral knee joint prosthesis has been implanted to enable access to the intramedullary canal of the femur without removing the femoral knee joint prosthesis from the femur.

In yet another preferred embodiment, a knee joint prosthesis that provides access to an intramedullary canal of a femur after the knee joint prosthesis has been implanted includes a femoral component and a seal member. The femoral component has at least a first bearing surface and defines a bore passing through the femoral component. The seal member substantially seals the bore in the femoral component, such that the seal member may be substantially removed after the femoral component is implanted to enable access to the intramedullary canal of the femur without having to remove the knee joint prosthesis from the femur.

In another preferred embodiment, a knee joint prosthesis system for enabling access to an intramedullary canal of a femur includes a femoral component and a removal instrument. The femoral component has at least a first bearing surface and a seal member that is operable to substantially seal an opening passing through the femoral component. The removal instrument is operable to engage the seal member to substantially remove the seal member from the femoral component to enable access to the intramedullary canal of the femur without having to remove the femoral knee joint prosthesis from the femur.

In an additional preferred embodiment, a method for enabling access to the intramedullary canal of a femur through a femoral knee joint prosthesis includes implanting a femoral knee joint prosthesis having a seal member which substantially seals an opening passing through the femoral knee joint prosthesis. A removal instrument is provided which is operable to engage the seal member. The seal member is substantially removed from the femoral knee joint prosthesis upon engaging the seal member with the removal instrument after the femoral knee joint prosthesis has been implanted to enable access to the intramedullary canal of the femur without removing the femoral knee joint prosthesis from the femur.

Use of the present invention provides a method and apparatus for enabling access to an intramedullary canal of a femur through a femoral knee joint prosthesis. As a result, the aforementioned disadvantages associated with the currently available "opened box" and "closed box" femoral knee joint prostheses have been substantially reduced or eliminated.

BRIEF DESCRIPTION OF THE DRAWINGS

Still other advantages of the present invention will become apparent to those skilled in the art after reading the following specification and by reference to the drawings in which:

FIG. 1 is a sagittal elevational view of a right knee joint having a knee joint prosthesis according to the teachings of a first preferred embodiment of the present invention;

FIG. 2 is a coronal elevational view of the knee joint prosthesis shown in FIG. 1;

FIG. 3 is a top view of the femoral component and a seal member of the knee joint prosthesis shown in FIG. 1;

FIG. 4 is a sectional view of the femoral component and seal member shown in FIG. 3 taken along line 4—4 in FIG. 3;

FIG. 5 is a top view of a seal member according to the teachings of a second preferred embodiment of the present invention;

FIG. 6 is a bottom view of the seal member shown in FIG. 5;

FIG. 7 is a partial top view of a femoral component and the seal member according to the teachings of the second preferred embodiment of the present invention;

FIG. 8 is a sectional view of the assembled femoral component and seal member shown in FIG. 7, taken along line 8—8 in FIG. 7;

FIG. 9 is a perspective view of a femoral component and seal member according to the teachings of a third preferred embodiment of the present invention;

FIG. 10 is a partial top view of the femoral component and seal member shown in FIG. 9;

FIG. 11 is a sectional view of the femoral component and seal member taken along line 11—11 in FIG. 10;

FIG. 12 is a perspective view of a femoral component and seal member according to the teachings of a fourth preferred embodiment of the present invention;

FIG. 13 is a sectional view of the femoral component and seal member shown in FIG. 12 taken along line 13—13 in FIG. 12;

FIG. 14 is a top view of a femoral component and seal member according to the teachings of a fifth preferred embodiment of the present invention;

FIG. 15 is a sectional view of the femoral component and seal member shown in FIG. 14 taken along line 15—15 of FIG. 14;

FIG. 15A is an enlarged sectional view of the femoral component and seal member shown in FIG. 15 taken about line 15A of FIG. 15;

FIGS. 16A–16B illustrate a method of implanting a femoral nail using the femoral component and seal member according to the teachings of the first preferred embodiment of the present invention;

FIG. 17 is a top view of a femoral component according to the teachings of a sixth preferred embodiment of the present invention;

FIG. 18 is a sectional view of the femoral component of FIG. 17 taken along line 18—18 of FIG. 17;

FIG. 19 is a bottom view of a seal member according to the teachings of the sixth preferred embodiment of the present invention;

FIG. 20 is a bottom view of a seal member according to the teachings of a seventh preferred embodiment of the present invention;

FIG. 21 is a sectional view of the femoral component and seal member of FIG. 20 taken along line 21—21 of FIG. 20;

FIG. 22 is a bottom view of a seal member according to the teachings of an eighth preferred embodiment of the present invention;

FIG. 23 is a bottom view of the seal member of FIG. 22 shown engaged with a retracting instrument;

FIG. 24 is a bottom view of a seal member according to the teachings of a ninth preferred embodiment of the present invention;

FIG. 25 is a partial bottom view of the femoral component and seal member according to the teachings of the ninth preferred embodiment of the present invention;

FIG. 26 is a sectional view of the femoral component and the seal member of FIG. 25 taken along line 26—26 of FIG. 25;

FIGS. 27A–27D illustrate a method for converting a non-stemmed femoral component according to the teachings of the eighth preferred embodiment of the present invention to a stemmed femoral component;

FIG. 28A is a perspective view of a femoral component and seal member according to the teachings of a tenth preferred embodiment of the present invention;

FIG. 28B is a sectional view of a femoral component and seal member taken along line 28—28 in FIG. 28A;

FIG. 29 is a perspective view of a femoral component and seal member according to the teachings of an eleventh preferred embodiment of the present invention;

FIG. 30 is a perspective view of a femoral component and seal member according to the teachings of a twelfth preferred embodiment of the present invention;

FIG. 38 is an enlarged cross sectional view of a distal end of the engagement instrument shaft and retaining shaft engaging the seal member taken about line 38—38 of FIG. 34;

FIG. 41 is an unassembled view of a removal portion of the removal instrument according to the teachings of the thirteenth preferred embodiment of the present invention;

FIG. 42 is an assembled perspective view of the removal portion shown in FIG. 41;

FIG. 45 is an exploded perspective view of a femoral component and a seal member according to a fourteenth embodiment of the present invention.

FIG. 46 a superior elevational view of the seal member according to the fourteenth embodiment of the present invention; and FIG. 47 is a cross-sectional view of the seal member in FIG. 46 taken along line 47—47.

DETAILED DESCRIPTION OF THE PREFERRED EMBODIMENTS

Figure 31:
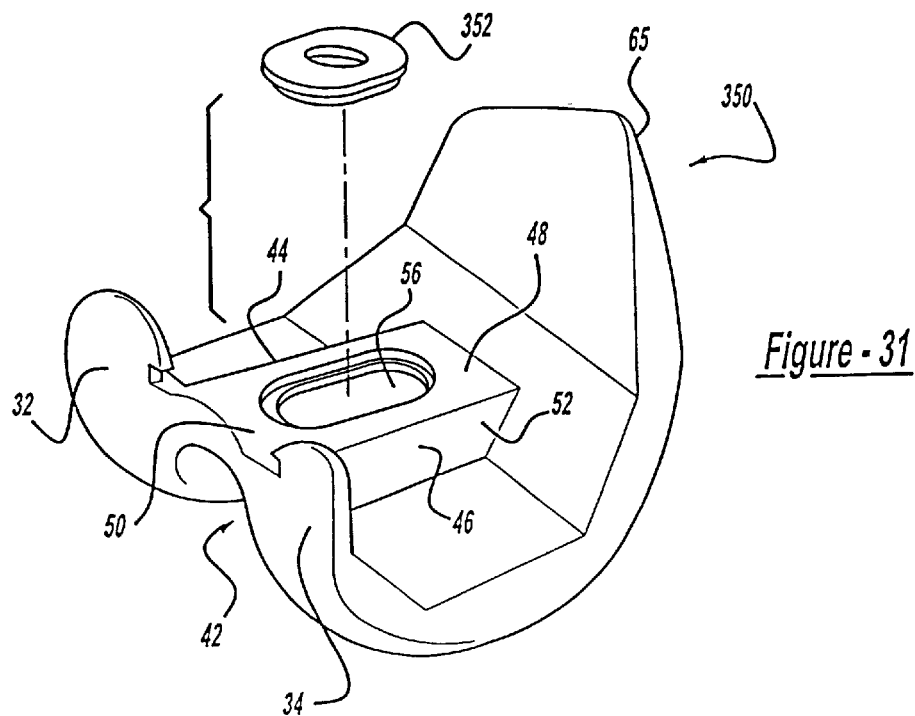
FIG. 31 is a perspective view of a femoral component and seal member according to the teachings of a thirteenth preferred embodiment of the present invention.

The following description of the preferred embodiments concerning a method and apparatus for gaining access to an intramedullary canal of a femur through a femoral knee joint prosthesis are merely exemplary in nature and are not intended to limit the invention or its application or uses. Moreover, while the present invention is described in detail below with reference to specific types of knee joint prostheses, it will be appreciated by those skilled in the art that the present invention is clearly not limited to only the specific type knee joint prostheses mentioned herein and may be applied to various other knee joint prostheses.

Referring now to FIGS. 1 and 2, there is shown a knee joint prosthesis 10 in accordance with a first preferred embodiment of the present invention. The knee joint prosthesis 10 is functionally depicted as being secured to a tibia 12 and a femur 14 of a surgically resected right knee joint, with the tibia 12 and femur 14 being shown in phantom. It will be understood that while the knee joint prosthesis 10 is suited for implantation into a right knee joint, a suitable left knee joint prosthesis can be similarly constructed. Moreover, it will also be understood that each of the embodiments disclosed herein have the same overall configuration as shown in FIGS. 1 and 2.

The knee joint prosthesis 10 is generally known as a posterior stabilized (PS) knee joint prosthesis 10 which is designed to provide adequate stability in case of moderate deterioration and instability of the human knee. This most typically occurs when the anterior and posterior cruciate ligaments are sacrificed or dysfunctional and the medial and lateral collateral ligaments remain functionally intact. The knee joint prosthesis 10 includes a femoral component 16 and a tibial component 18. The knee joint prosthesis 10 may be based upon any closed box or opened box knee joint prosthesis, such as that disclosed in U.S. Pat. No. 5,330,534, which is hereby incorporated by reference. The knee joint prosthesis 10 may also be based upon the "Performance® Total Knee System", "Ascent™ Total Knee System", "AGC® Tradition Total Knee System" or the "Maxim Complete Knee System" each available from Biomet, Inc. of Warsaw, Ind. In other words, it is to be understood that the knee joint prosthesis 10 may be based upon various knee joint prosthetic platforms and be designed to include the various features of the preferred embodiments of the present invention.

Generally, the tibial component 18 is adapted to be secured to the proximal end of the tibia 12 after the tibia has been resected in a manner well known in the art. The tibial component 18 includes a platform like tibial tray 20 and an inferiorly extending tibial stem 22. The tibial stem 22 is adapted to be received in a corresponding opening made by the surgeon in the longitudinal center of the tibia 12. The tibial stem 22 may include a bore passing therethrough which is able to receive a suitable support member which is secured to the tibia 12 in a manner well known in the art. Should additional fixation be required, holes can be provided in the tibial tray 20 through which bone screws may be passed to secure the tibia tray 20 to the end of the tibia 12. The tibial tray 20 and stem 22 is preferably manufactured from Ti-6Al-4V or any other suitable biocompatible material.

Positioned atop the tibial tray 20 is a tibial insert 24. The tibial insert 24 is preferably formed from a surgical grade, low friction, low wearing plastic, such as UHMWPE or other suitable materials. The tibial insert 24 includes a stabilizing post 26 and first and second articulating or bearing regions 28 and 30 which articulate with the femoral component 16. The tibial insert 24 is secured to the tibial tray 20 by any suitable means. It should be noted that the only limitation the tibial component 18 places on the femoral component 16 is that the stabilizing post 26 be cleared by the femoral component 16.

The sealable convertible femoral component 16 generally includes a first condylar portion 32 and a second condylar portion 34 which have a first femoral bearing surface 36 and a second femoral bearing surface 38, respectively. The first and second condylar portions 32 and 34 of the femoral component 16 are interconnected by an inner condylar portion 40 which defines an inner condylar recess 42. The inner condylar portion 40 defining the inner condylar recess 42 includes a first lateral sidewall 44 and a second lateral sidewall 46 which are planar and substantially parallel to each other. The anterior portions of the first and second lateral sidewalls 44 and 46 are connected by an anterior wall 48 and the posterior portions of the first and second lateral sidewalls 44 and 46 are connected by a posterior wall 50. The inner condylar portion 40 which includes the first and second lateral sidewalls 44 and 46 and the anterior and posterior walls 48 and 50 define the perimeter of a box 52 that defines the inner condylar recess 42.

Positioned atop the box 52 is a substantially planar integral top 54 which defines an opening or bore 56. The opening 56 is defined by opposed planar parallel sidewalls 58 and 60 and arcuate anterior and posterior endwalls 62 and 64, respectively. The femoral component 16 including the box 52 is preferably formed as a unitary structure and preferably cast of a biocompatible high strength alloy such as a cobalt-chromium-molybdenum alloy or other suitable material. All surfaces which do not contact the femur 14 are preferably highly polished. The femoral component 16 further includes an arcuate patellar portion 65 which is disposed on the anterior surface of the femoral component 16. The patellar portion 65 is shaped to allow anatomical tracking of a natural or prosthetic patella. The patella prostheses which are compatible with the present invention may be of varying shapes such as round, oval or dome shaped and may be constructed from polyethylene, polyethylene with metal backing, or other suitable materials.

In order to substantially seal, close or cover the opening 56 in the top 54 of the box 52 such that the box 52 may be subsequently opened or breached after implantation of the femoral component 16, a convertible seal member 66 is provided. The seal member 66 is substantially rectangular in shape and formed from polymethylmethacrylate (PMMA) which is a transparent material or any other suitable material having any other suitable shape. The seal member 66 is secured to the top 54 of the box 52 by use of an adhesive or other appropriate securing mechanism further discussed herein. The seal member 66 is preferably 1–2 mm thick and provides a substantially fluid tight seal atop the box 52. However, it should be noted that the seal member 66 does not have to provide a fluid tight seal and merely needs to close or cover most of the opening 56. In other words, the seal member 66 may be made out of a screen or mesh material or not necessarily be sealed around the entire periphery of the opening 56. Since the seal member 66 is formed from PMMA, the seal member may be opened or breached subsequent to implantation of the femoral component 16 should access to the intramedullary canal of the femur 14 be required.

The seal member 66 may be opened or breached by any appropriate means such as drilling, puncturing or by simply driving a femoral nail directly through the seal member 66 in the case of repairing a supracondylar fracture. The seal member 66 closes or seals the box 52 and provides the surgeon with a substantially transparent window through opening 56 which can be used to assist in the implantation of the femoral component 16. The closed box 52, via the seal member 66 further provides and prevents bone cement or other debris from entering the articulating joint area between the femoral component 16 and the tibial component 18. Should it be subsequently required to obtain access to the intramedullary canal of the femur 14, the femoral component 16 does not require removal and the convertible seal member 66 may simply be breached by any appropriate means. Any debris caused from this breach will not pose a problem since the seal member 66 is made from PMMA, which is bone cement material and consistent with normal preparation.

Turning to FIGS. 5–8, a second preferred embodiment of a sealable convertible femoral component 67 is shown which utilizes a seal member 68. In this regard, like reference numerals will be used to identify like structures. The seal member 68 includes a top planar surface 70 defined by first and second planar and substantially parallel sidewalls 72 and 74 and anterior and posterior arcuate sidewalls 76 and 78. The sidewalls 72 and 74 meet or extend out substantially to lateral sidewalls 44 and 46, while arcuate sidewalls 76 and 78 extend out beyond arcuate sidewalls 62 and 64. Positioned about the underside 80 of the seal member 68 is a stepped shoulder 82 which extends substantially about the periphery of the seal member 68. The stepped shoulder 82 defines a region 84 which substantially mates within the opening or bore 56. The region 84 includes sidewalls 86 and 88 and a posterior arcuate sidewall or endwall 90 which are substantially perpendicular to the planar underside 80 that forms a recessed geometry. An anterior arcuate sidewall or endwall 92 angles inward at an angle of about 60 degrees, identified by reference numeral 94. This angled sidewall 92 mates with the corresponding anterior endwall 62 which is machined or cast to have a mating angular surface for this embodiment.

The seal member 68 is mated with the femoral component 67 by first inserting the anterior sidewall 92 of the seal member 68 adjacent the anterior sidewall 62 of bore 56. Once aligned, the posterior portion of the seal member 68 is tilted downward into position such that the stepped shoulder 82 mates with a stepped cutout region 96 formed about the bore 56 in the femoral component 67. This provides mechanical securement or a mechanical connection mechanism between the seal member 68 and to the femoral component 67, shown in FIG. 8. To provide a fluid tight seal, an adhesive may be applied between the stepped shoulder 82 on the seal member 68 and the cutout region 96 machined into the top 54 of the box 52. The top 70 of the seal member 68 is shown substantially flush with the top 54 of the box 52 and the underside or bottom 80 is substantially flush with the underside 98 of the box 52. However, the top 70 of the seal member 68 may also be raised (up to 50–70 mm) to accommodate for a constrained post on the tibial component 18.

Here again, the seal member 68 is formed from PMMA and, thus, provides a transparent window through the top of the box 52 or other suitable material. As with the seal member 66, the seal member 68 may be opened or breached by drilling, piercing, etc. after the femoral component 67 has been implanted onto the femur 14 should it be required to gain access to the intramedullary canal of the femur 14. Alternatively, the seal member 68 may be formed from a temperature dependent material or from two types of material, one of which is temperature dependent. In other words, the seal member 68 may be formed such that when the seal member 68 is warmed to a temperature similar to body temperature, the seal member 68 expands to be secured within the top of the box 52 such that when the material is cooled, it retracts or contracts to be removed from the top of the box 52. Still further, the seal member 68 may be formed from a material that reacts with certain chemicals such that the adhesive or a portion of the seal member 68 may be removed or dissolved upon reacting with another component applied to the seal member 68. This will also enable the seal member 68 to be easily removed. Finally, the seal member 68 may be formed from a high density polyethylene and thermo-mechanically bonded over the opening 56 in the box 52.

Referring now to FIGS. 9–11, a third preferred embodiment of a sealable convertible femoral component 100 is shown with a seal member 102. Here again, like reference numerals will be used to describe like structures. In this regard, the box 52 of the femoral component 100 includes the top 54 defining the bore 56. The top 54 defines a cutout region 104 having opposed anterior and posterior angled sidewalls or endwalls 106 and 108 which angle downward at about 45 degrees (45°) relative to the top 54 or at any other appropriate angle that is less than 90° or greater than 0°. The depth of the cutout region 104 is substantially equal to the thickness of the seal member 102. The seal member 102 is again formed from PMMA and includes first and second planar parallel sidewalls 110 and 112 and angled anterior and posterior sidewalls or endwalls 114 and 116, respectively. The seal member 102 further includes a pair of bores 118 passing through a top 120 of the seal member 102 which are in communication with elongated oval chambers or pockets 122.

The underside 124 of the seal member 102 slidably mates with the cutout region 104, as the anterior and posterior sidewalls 114 and 116 mechanically communicate with angled anterior and posterior sidewalls 106 and 108. This provides a mechanical connection mechanism to create mechanical securement which prevents the seal member 102 from being pushed outward substantially perpendicular to the top 54 when a force is applied to the underside 124 to breach or open the seal member 102. To provide further mechanical securement of the seal member 102 atop the box 52, an appropriate adhesive can be injected through bores 118, thereby flowing into elongated oval pockets 122. Additionally, adhesive may be thinly applied to the top of the cutout region 104 and the angled sidewalls 106 and 108 before slidably receiving the seal member 102. Alternatively, pins, screws or other attachment mechanisms may also be used.

The third embodiment of the femoral component 100 having the seal member 102 operates in substantially the same manner as the first and second preferred embodiments. In this regard, the seal member 102 may be opened or breached by any suitable means, such as drilling, puncturing, etc. to enable access to the intramedullary canal of the femur 14. Access to the intramedullary canal would generally be required should there by a supracondylar fracture of the femur 14, thereby requiring a femoral nail to stabilize the femur 14.

FIGS. 12–13 illustrate a fourth preferred embodiment of a sealable convertible femoral component 126 having a seal member 128. In this regard, like reference numerals will be used to identify like structures with respect to the previous preferred embodiments of the present invention. Here again, the seal member 128 is formed from a PMMA or other suitable biocompatible material and includes laterally spaced planar parallel sidewalls 130 and 132 which mate with sidewalls 44 and 46. The seal member 128 further includes a planar anterior sidewall 134 and a planar posterior sidewall 136 having notched corners or angled sidewalls 138.

In this embodiment, the top 54 of the box 52 is substantially planar and defines the bore 56. The box 52 includes the lateral sidewalls 44 and 46 and the anterior inner condylar portion 40 defines an anterior slot 140 which is operable to nestingly receive the anterior sidewall 134 of the seal member 128. The posterior inner condylar portion 40 also defines a pair of notches 142 which extend adjacent the first and second condylar portions 32 and 34. The notch regions 142 are operable to nestingly and snappingly receive the angled sidewalls 138 adjacent the posterior sidewall 136 of the seal member 128 or the notch regions 142 can also slidably receive the seal member 128 from the posterior side.

The seal member 128 is installed by first engaging the anterior sidewall 134 of the seal member 128 with the anterior slot 140 of the femoral component 126. An adhesive may first be applied to the top 54 of the box 52 should this be desired. Once the anterior sidewall 134 is engaged within the anterior slot 140, the posterior angled sidewalls 138 are tilted into engagement with the femoral component 126 until the angled sidewalls 138 are snapped in place beneath the posterior notches 142 to provide mechanical securement. Since the seal member 128 is made from PMMA, the seal member 128 is able to be slightly flexed, enabling the seal member 128 to be snapped in place and secured within anterior and posterior grooves or slots 140 and 142, respectively. Here again, the seal member 128 may be used similar to the seal members set forth in the first, second and third embodiments. In this regard, the seal member 128 may be readily breached or opened should access be required to the intramedullary canal of the femur 14 after the femoral component 126 has already been implanted.

FIGS. 14 and 15 illustrate a fifth preferred embodiment of a sealable convertible femoral component 144 employing a seal member 146. In this regard, like reference numerals will be used to identify like structures with respect to the previous preferred embodiments of the present invention. The top 54 of the box 52 defining the bore 56 includes a stepped counterbore 148 extending substantially about the periphery of the bore 56. The seal member 146 is sized to substantially mate with the counterbore region 148 when the seal member 146 is nestingly received within the top 54. The seal member 146 is preferably formed from a thin metallic foil such as cobalt-chromium-alloy, having a thickness of about 0.01 mm–0.025 mm. The seal member 146 is secured to the femoral component 144 atop the box 52 by means of a weld 150 which extends substantially about the periphery of the bore 56. Alternatively, the seal member 146 may be cast directly into the femoral component 144. In other words, the seal member 146 would simply be a thinned region (0.01 mm–0.25 mm) formed directly from a casted femoral component 144 and having substantially the same structure and function as described above.

Since the seal member 146 is formed from a thin metallic foil or area, the seal member 146 will have a higher impact resistance as compared to seal members made from PMMA. The seal member 146 may be opened or breached simply by puncturing the underside 152 of the seal member 146 either with an appropriate tool or by simply driving the end of a retrograde nail up through the seal member 146 after the femoral component 144 has already been implanted. The seal member 146 may also have a V-shaped depression 151 formed within the seal member 146 about its periphery that allows it to be easily peeled open or away. The V-shaped depression 151 can be engaged by a tool fashioned to engage the depression 151 to peel the seal member 146 out of the bore 56.

Turning to FIGS. 16A and 16B, a method for enabling access to an intramedullary canal 154 of the femur 14 will now be described in detail with respect to the first preferred embodiment of the femoral component 16. However, it will be understood by those skilled in the art that this method, or any other method of opening or breaching the particular seal member used may be employed with any of the embodiments discussed herein. First, after the femoral component 16 has been implanted onto the femur 14 using techniques well known in the art, there may be a necessity to gain access to the intramedullary canal 154 of the femur 14 should a supracondylar fracture 156 occur with the patient. In such a case, the femoral component 16 does not require removal from the femur 14 and the convertible sealed box 52 may simply be opened, exposed or breached by any appropriate means. In this example, a drill bit 158 driven by a driver 160 is employed to bore an access hole through the PMMA seal member 66. Since the seal member 66 is formed from PMMA, debris does not pose a problem. Once an opening 162 is created in the seal member 66 through the box 52 and the intramedullary canal 154 by drilling or reaming, the drill 158 is removed from the box 52, and a femoral nail 164 is driven through the opening 162 in the box 52 upward into the intramedullary canal 154 of the femur 14.

The femoral nail may be any conventional femoral nail, such as that provided by Biomet of Warsaw, Ind. and referred to as a "Biomet Retrograde Femoral Nail". The femoral nail 164 includes a rounded end 166 and a blunt end 168. Passing laterally through the femoral nail 164 is a pair of distally positioned threaded anchor screws 170 that extend through a bore 172 and an elongated bore 174. A pair of proximally positioned threaded anchor screws 175 pass through bores 176 and are substantially rotated 90 degrees (90°) relative to screws 170. As shown in FIG. 16B, the femoral nail 164 longitudinally extends through the intramedullary canal 154 substantially through and along the supracondylar fracture 156 and into dense cortical bone region 178 to provide overall stability of the fractured femur 14. With the femoral nail 164 in place, the tibial component 18 is subsequently mated with the femoral component 16 in a conventional articulating manner. The surgery is completed without having to remove the femoral component 16. Such a procedure substantially reduces surgical time, cost and complexity, as well as reduces the patient's recovery time.

Turning to FIGS. 17–19, a mechanically sealable convertible femoral component 180 according to the teachings of a sixth preferred embodiment of the present invention is shown. In this regard, like reference numerals will be used to identify like structure with respect to the other preferred embodiments of the present invention. The femoral component 180 includes the box 52 having top 54 which defines bore 56. The sidewalls 58 and 60 of the bore 56 extend to the inner lateral sidewalls 44 and 46 which define channels 182, shown clearly in FIG. 18. The lateral sidewalls 44 and 46 are also slightly thicker than in the first preferred embodiment.

A seal member 184 having a mechanical securing mechanism 186 is shown in FIG. 19 and is sized to be matingly received within bore 56. In this regard, the seal member 184 includes a substantially planar seal plate 187 having a pair of geared racks 188 that include teeth 190 that mate with a pinion gear 192 having teeth 194. The rack members 188 include a pair of latch members 196 which extend substantially perpendicular to the rack members 188. Upon rotating the pinion 192, via a hex drive 198, the teeth 194 of the pinion 192 engage the teeth 190 of the rack 188, thereby enabling the latches 196 to be extended or retracted relative to the seal member 184 as they slide beneath retaining members 200. To maintain the rack member 188 in an extended position, a catch 189 formed from a spring biased pin 191 holds one rack member 188 in an extended position, which also holds the other rack member 188 in an extending position. Thus, the latch 189 must also be disengaged, via the hole 193 in the pin 191, to move the rack members 188. All of the components of the seal member 184 are made from a biocompatible material such as cobalt-chromium-alloy.

The seal member 184 is installed by rotating the pinion 192 counterclockwise, via the hex drive 198, using an appropriate hex head wrench to retract the latch members 196 within the outer periphery of the seal plate 187. Once retracted, the seal member 184 is slidably received between the lateral sidewalls 44 and 46 until the latch members 196 are aligned with channels 182. Once aligned, the pinion 192 is again rotated clockwise with an appropriate hex head wrench, thereby extending the latch members 196 within channels 182 to securely retain the seal member 184 atop and within the box 52.

Should access to the intramedullary canal be required to repair a supracondylar fracture, the seal member 184 is simply removed, via rotating the pinion 192 counterclockwise, thereby disengaging the latches 196 from within the channels 182 and simply removing the seal member 184 from between the lateral sidewalls 44 and 46. Alternatively, should the patient be exhibiting instability after the PS femoral component 180 is implanted and it is desired to provide a fully constrained femoral component 180, additional stabilization of the femoral component 180 is required, via an axially extending intramedullary stem which is coupled to the femoral component 180. In this case, such a stem can be mounted on the top of the seal member 184 and installed by simply removing the seal member 184 without the stem and engaging a new seal member with the stem, as further discussed herein.

Referring to FIGS. 20–21, a sealable convertible femoral component 202 according to the teachings of a seventh preferred embodiment of the present invention is shown. In this regard, like reference numerals will be used to identify like structures. The femoral component 202 is substantially similar to the femoral component 180 except that the channels 182 are positioned further downward from the top 54 of the box 52. A seal member 204 is shown having a mating seal plate 206 which is snuggly received within the bore 56 and a mechanical securing mechanism 207. Positioned on the underside of the seal plate 206 are a pair of slidable latches 208 which are slidably secured under stepped brackets 210 which are welded to the underside of the seal plate 206. Each latch member 208 has a planar engagement sidewall 212 and an arcuate engagement sidewall 214 that has a slightly angled sidewall which angles at about 4° or less (self-locking). Each arcuate angled sidewall 214 slidably engage a conical plug 216 which forms a Morse-type taper and acts as a wedge mechanism. Alternatively, the conical plug 216 and the latches 208 may be threaded and threadably engage one another.

In other words, to install the seal member 204 within the femoral component 202, the wedge or plug 216 is removed from the seal member 202 by threadably engaging a threaded bore 218 with an appropriate removal tool and slidably retracting the latch members 208. Once retracted, the seal member 204 is slidably positioned between the sidewalls 44 and 46 to align the latch members 208 with the channels 182. Once aligned, the channel members 208 are slid apart from one another such that the engaging sidewalls 212 are nestingly received within the channels 182. Once engaged, the plug or wedge 216 is positioned between and against the angled arcuate sidewalls 214. The plug 216 is then impacted or threaded with an appropriate instrument until a bottom surface 219 of the plug 216 comes to rest atop the seal plate 206, thereby securing the seal member 204 within the femoral component 202. Should it be desired to gain access to the intramedullary canal of the femur 14, a removal tool is simply threadably received within threaded bore 218 of plug 216 and impacted away from the seal plate 206 to remove the plug 216. Once removed, the latch members 208 are retracted from the channels 182 and the seal member 204 is removed from the femoral component 202.

In FIGS. 22 and 23, an eighth preferred embodiment of a seal member 220 is shown which may be used with the femoral component 180 of FIG. 17. In this regard, the seal member 220 includes a seal plate 222 and a mechanical sealing member 223 having a pair of opposed latch members 224. The latch members 224 are slidably retained by stepped slide members 226 that are welded to the underside of seal plate 222. Each latch member 224 includes a planar engagement sidewall 228 and an inner arcuate sidewall 230. The planar sidewall 228 is operable to engage the channel 182, and the inner arcuate sidewall 230 enables access through the center of the seal plate 222, further discussed herein. Each latch member 224 further includes a pair of engagement pins 232 which retain a pair of resilient springs 234. The springs 234 are used to outwardly bias the latch members 224, as shown in FIG. 22.

In order to retract the latch members 224, a pair of opposed bores 236 are provided which may be engaged by a removal tool 238. To retract the latch members 224, a pair of posts 240 extending from the removal tool 238 are simply inserted within the bores 236 while the handle 242 is drawn together about pivot 244. With the latch members 224 fully retracted, the seal member 220 may be installed within the femoral component 180. Once the latch members 224 are aligned with the channel 182, the handle 242 is slowly released to allow the spring biased latches 224 to be nestingly received within the channels 182. It should further be noted that the arms 246 of the tool 238 are stepped to provide clearance for the tool 238 to extend within the interior of the box 52 that defines the inner condylar recess 42.

Referring to FIGS. 24–26, a ninth preferred embodiment of a sealable convertible femoral component 250 having a seal member 252 is shown. Here again, like reference numerals will be used to identify like structures. The femoral component 250 is substantially similar to the other femoral components, except that the elongated bore 56 is replaced with a circular bore 254 which passes through the top 54 of the box 52 and the sidewalls 44 and 46 are thicker in construction. The seal member 252 includes a mechanical securing mechanism 255 having a stepped cylindrical region 256 that extends from a seal plate 258 and is aligned with the bore 254. The cylindrical step portion 256 includes a cylindrical sidewall 260 and a hexagonal shaped bore 262 which is operable to be engaged with an appropriate hex head tool. The seal plate 258 includes a pair of opposed arcuate shaped wings 263 having arcuate sidewalls 264.

A semicircular channel 266 is formed within sidewalls 44 and 46, as well as anterior sidewall 48, as shown in FIG. 25. This semi-circular channel or slot 266 enables the seal member 252 to be substantially rotated, while wing members 263 nestingly and slidably engage the semi-circular channel 266. To install the seal member 252 within the femoral component 250, the seal member 252 is aligned between the sidewalls 44 and 46. With the wing members 263 aligned substantially along the semi-circular channel 266, the seal member 252 is rotated clockwise about 90 degrees (90°) until sidewall 268 engages edge 270 formed within sidewall 266, via a hex head drive engaging the bore 262. To remove the seal member 252, the seal member 252 is simply rotated counterclockwise until the wing members 263 are aligned between the sidewalls 44 and 46.

The seal members 184, 204, 220 and 252 shown in FIGS. 17–26 mechanically seal the top 54 of the box 52 in each of the particular femoral components. Each of the seal members 184, 204, 220 and 252 may be employed should a supracondylar fracture occur and a femoral nail be required to be inserted within the intramedullary canal of the femur 14. In this way, the particular seal member is simply mechanically removed as previously discussed and a femoral nail is simply passed through the bore 56 in the opened box 52. These embodiments may also be used to upgrade the particular femoral component from a posterior stabilized (PS) femoral component to a stemmed femoral component. In other words, with a stemmed femoral component, further support of the femoral component is required and thus, the femoral component requires a stem that extends up into the intramedullary canal. A method for gaining access to the intramedullary canal and modifying the posterior stabilized (PS) femoral component to a stemmed femoral component is shown in FIGS. 27A–27D.

FIGS. 27A–27D illustrate a method for converting the posterior stabilized (PS) femoral component 180 that employs the seal member 220 to a stemmed femoral component 180. It will also be understood by those skilled in the art that any of the embodiments shown in FIGS. 17–26 may be modified to include a drill guide and stem component as discussed herein. In this regard, the femoral component 180 having the sealed box 52 is first opened upon engaging the posts 240 of the retraction tool 238 within bores 236 of the seal member 220. Once engaged, the handle 242 is drawn together, thereby retracting the latch members 224 and enabling the removal of the seal member 220 from within the top of the box 52 and out from between the lateral sidewalls 44 and 46.

Once removed, a drill guide 274 may be installed within the femoral component 180, via engaging the pair of channels 182, using an identical mechanical engagement mechanism 223 as used with the seal member 220. The drill guide 274 includes a guide member 276 defining a guide bore 277 which may be used to guide a drill bit 278 driven by a driver 280 into the femur 14 (see FIG. 27B). A cavity 282 is then formed, via the drill 278, which is operable to slidably receive a stem, further discussed herein. Once the cavity 282 is formed, the drill 278 is removed and the drill guide 274 is disengaged from the femoral component 182, via the tool 238, in a substantially similar fashion as the seal member 220 is removed.

Once the drill guide 274 is removed, a stemmed component 284 having a stem 286 is implanted into the femur 14 similar to the way the seal 220 closes the bore 56. In this regard, the stem component 284 includes the same engagement mechanism 223 in the seal member 220 and may simply be installed utilizing the tool 238. Alternatively, the seal member 220 may be modular in that the stem 286 may be removably coupled to the seal member 220 after the seal member 220 is removed from the femoral component 180. Once installed, the posterior stabilized (PS) femoral component 180 is modified to a stemmed femoral component 180. This procedure substantially eliminates the need to remove the existing femoral component 180 and replace it with a new femoral component by enabling the top 54 of the box 52 to be opened from the exposed side of the femoral component 180 and replaced with a stem component. This reduces overall surgical cost, complexity and time, as well as reducing the patient's recovery time.

Turning now to FIGS. 28A–28B, a tenth preferred embodiment of a sealable convertible femoral component 300 having a seal member 302 is shown. Here again, like reference numerals will be used to identify like structures. The femoral component 300 is substantially similar to the other femoral components, except that elongated channels or grooves 304 are formed into the lateral sidewalls 44 and 46, shown clearly in FIGS. 28B. The seal member 302 is again preferably formed by PMMA or other appropriate material such as UHMWPE. The seal member 302 includes a top 306 having rounded corners 308 and a pair of engagement members or elongated fingers 310 that snappingly engage grooves 304. The seal member 302 may be opened or breached by any appropriate means after the femoral component 300 has been implanted.

Referring to FIG. 29, an eleventh preferred embodiment of a femoral component 312 and seal member 314 is shown. In this regard, like reference numerals will be again used to identify like structures. The femoral component includes a plurality of bores 316 having enlarged counterbores 318 extending through the lateral sidewalls 44 and 46 adjacent the opening 56. The seal member 314 again includes a top surface 320 having rounded corners 322 along with a plurality of engagement members 324. Each engagement member 324 includes a substantially cylindrical sidewall 326 and a conical end 328 which are adapted to be snappingly received within bore 316 and counterbore 318, respectively. Again, the seal member 314 may be formed from PMMA, or any other appropriate material. Accordingly, the seal member 314 again may be opened by any appropriate means to gain access to the intramedullary canal of the femur 14 after the femoral component 312 has been implanted.

Turning to FIG. 30, a femoral component 330 and a seal member 332 according to the teachings of a twelfth preferred embodiment of the present invention is shown. The femoral component 330 includes four substantially rectangular bores 334 formed into the lateral sidewalls 44 and 46, each having a side opening 336. The seal member 332 again includes a top 338 having rounded corners 340 and four rectangular engagement members or legs 342. Each leg 342 includes a finger 344 extending therefrom which is operable to be snappingly received within and extend from side openings 336 of channels 334. Again, the seal member 332 may be formed from PMMA, or any other appropriate material and is operable to be opened or breached by any appropriate means.

FIGS. 31–43 illustrate a femoral component 350 and a seal member 352, along with a removal instrument 354 according to the teachings of a thirteenth preferred embodiment of the present invention. Here again, like reference numerals will be used to identify like structures of the femoral component 350. The femoral component 350 includes the first condylar portion 32, the second condylar portion 34 and the inner condylar portion 40 positioned therebetween. The inner condylar portion 40 again defines the inner condylar recess 42 which is specifically defined by the first lateral sidewall 44 and the second lateral sidewall 46, along with the anterior wall 48 and the posterior wall 50 which are each formed as a cam or lobe. These sidewalls define the perimeter of the box 52 having opening 56. The femoral component 350 also includes the patellar portion 65 which is shaped to allow anatomical tracking of a natural or prosthetic patella. Here again, the femoral component 350 is preferably formed as a unitary structure and preferably cast of a biocompatible high strength alloy, such as cobalt-chromium-molybdenum alloy or other suitable material.

Figure 32:
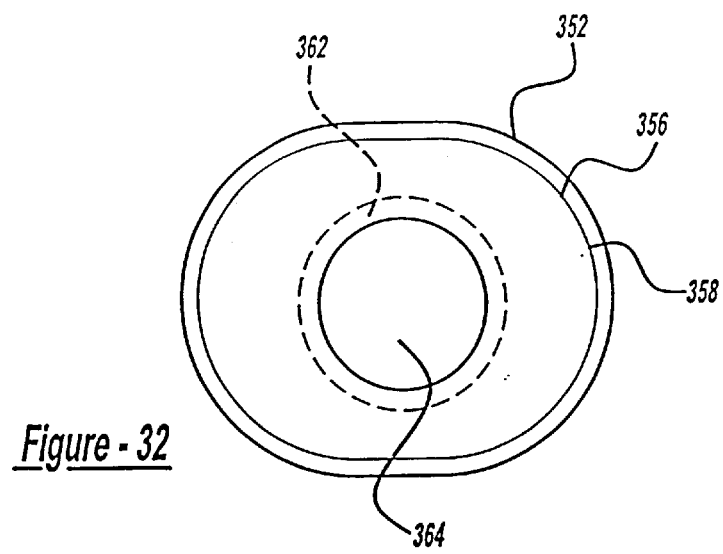
FIG. 32 is a top elevational view of the seal member according to the teachings of the thirteenth preferred embodiment of the present invention.

In order to close the opening 56 in the box 52, the removable seal member 352 is provided (see FIG. 32). The seal member 352 has an elongated oval shape defined by sidewall 356 and frangible lip 358. Seal member 352 further defines a circular tapered recess 360 defined by tapered sidewall 362 and planar wall 364. The seal member 352 is also preferably formed from cobalt-chromium-molybdenum or other suitable material. In order to removably secure the seal member 352 within the opening 56 in the box 52, the seal member 352 is welded to the stepped sidewall 366 defining the opening 56 by way of an electroned beam. This securement mechanism provides for a fluid-tight seal of the opening 56 and also enables the seal member 352 to be operably removed from the femoral component 350 by use of the removal instrument 354.

The removal instrument 354 is primarily comprised of two main portions. These portions include an engagement portion 368 and a removal portion 370. The engagement portion 368 is primarily comprised of three main components. These components include an engagement shaft 372, a retaining shaft 374 and a femoral engagement member 376.

The engagement shaft 372 is preferably formed from stainless steel and includes a proximal coupling portion 378 and a distal engagement portion 380 with an elongated shaft 382 located therebetween. The proximal coupling portion 378 includes an outer threaded sidewall 384 which is operable to be threadably engaged by the retaining shaft 374. The distal engagement portion 380 includes a tapered shoulder 386 and a planar distal end 388 which nestingly engages within the circular tapered recess 360 in the removable seal member 352. Passing through the engagement shaft 372 is a cylindrical bore 390 having a tapered shoulder 392 and an enlarged cylindrical sidewall 394. Four (4) channels 396 also extend through a portion of the elongated shaft 382 and through the distal engagement portion 380, such that the elongated channels 396 are in communication with the cylindrical bore 390. The elongated channels 396 enable the distal engagement portion 380 to resiliently compress to enable the tapered shoulder 386 to snappingly engage the tapered sidewall 362 in the removable seal member 352. Extending laterally out from the elongated shaft 382 is a substantially rectangular guide block 398 which is sized to slidably engage the first and second lateral sidewalls 44 and 46 of the box 52.

Figure 37:
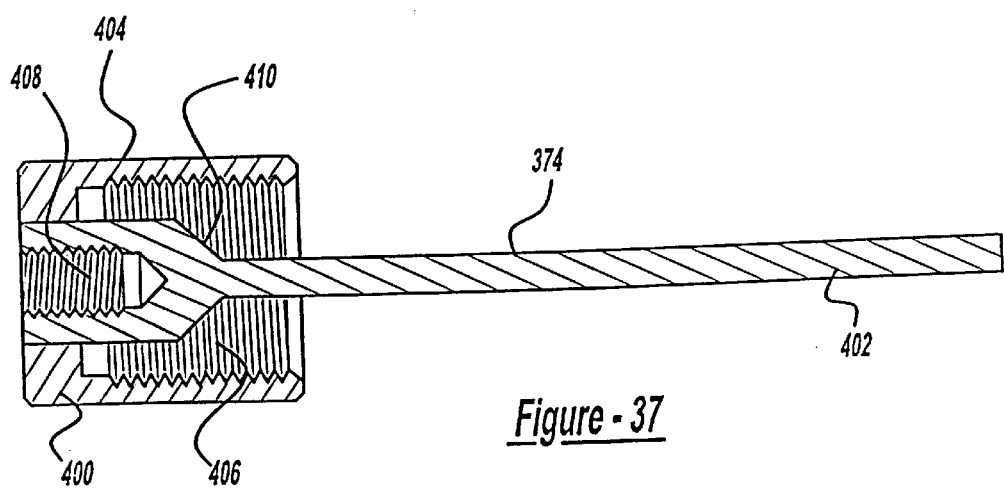
FIG. 37 is an elevational view of the retaining shaft according to the teachings of the thirteenth preferred embodiment of the present invention.

The retaining shaft 374, as shown in FIG. 37, includes a proximal coupling member 400 and a distally extending cylindrical shaft 402. Here again, the retaining shaft 374 is preferably formed from stainless steel or other appropriate material which may be readily sterilized. The coupling member 400 includes an outer cylindrical sidewall 404 and an internal threaded sidewall 406 which threadably engages the threaded sidewall 384 of the engagement shaft 372. The coupling member 400 also defines an internal threaded sidewall 408 which operably engages the removal portion 370 of the removal instrument 354, further discussed herein. Located within the coupling member 400 is a tapered shoulder 410 which is nestingly received within the tapered shoulder 392 of the engagement shaft 372. Referring briefly to FIG. 38, a cross-sectional view of the assembled engagement shaft 372, along with the retaining shaft 374 is shown engaging the seal member 352.

Figure 39:
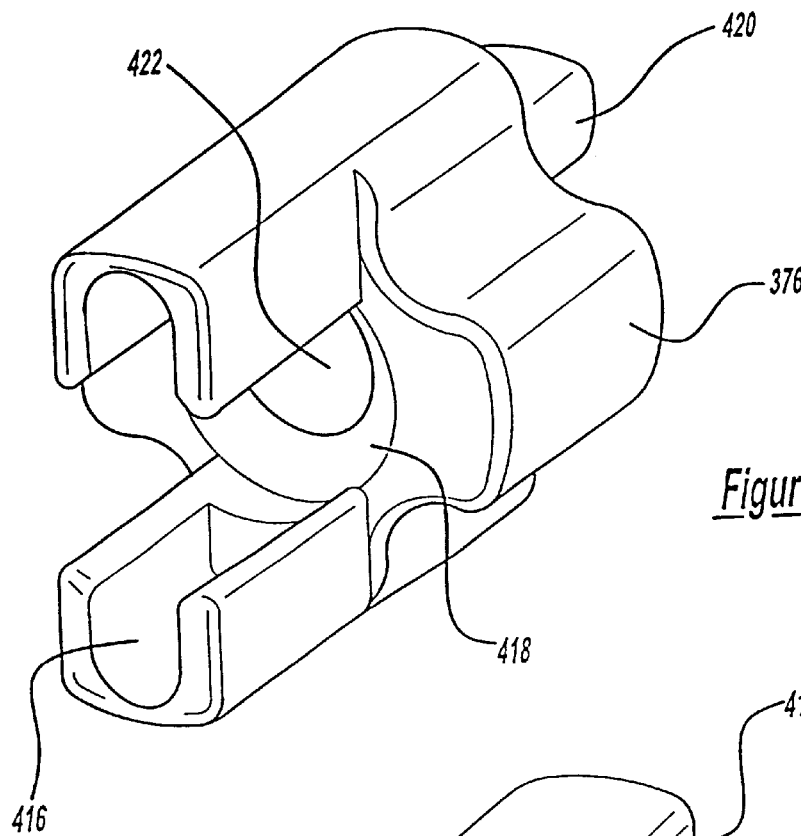
FIG. 39 is a perspective view of a proximal portion of an engagement member of the removal instrument according to the teachings of the thirteenth preferred embodiment of the present invention.
Figure 40:
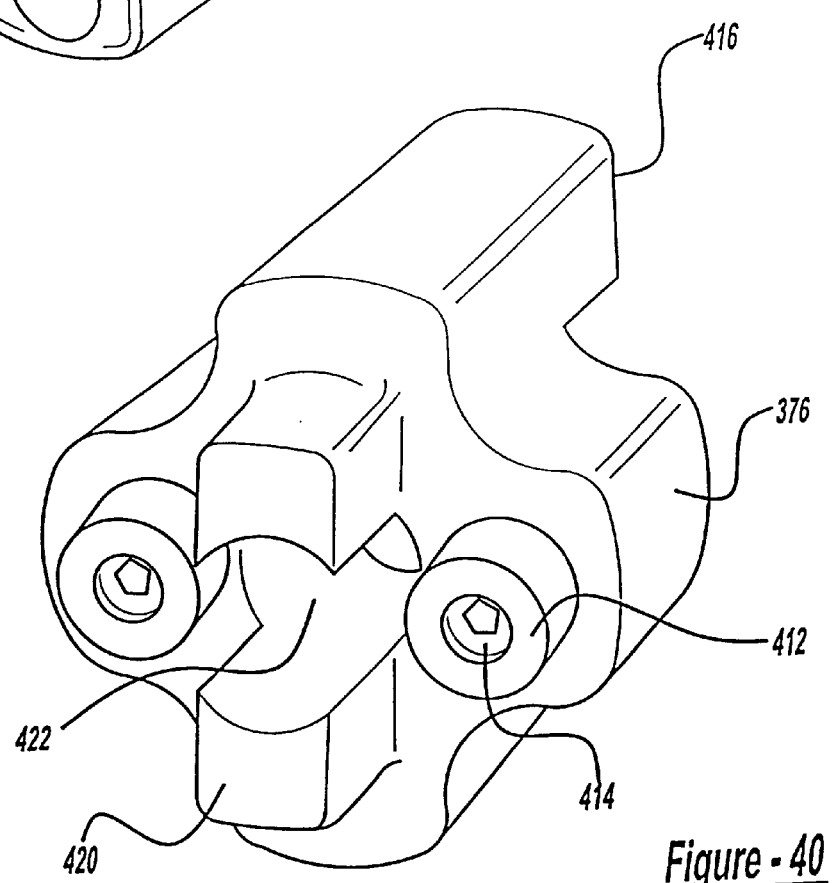
FIG. 40 is a perspective view of the distal end of the engagement member of the removal instrument according to the teachings of the thirteenth preferred embodiment of the present invention.

Turning now to FIGS. 39 and 40, the femoral engagement member 376 shown in further detail. The femoral engagement member 376 is preferably formed from aluminum or other appropriate material and includes a pair of polymer pads 412 which are secured to the engagement member 376 by way of threaded screws 414. The proximal end of the engagement member 376 defines a pair of opposed channels 416 which slidably receive the removal portion 370. The proximal end of the femoral engagement member 376 also defines a tapered shoulder 418 which slidably receives the proximal end of the assembled engagement shaft 372 and retaining shaft 374. Extending from the distal end of the engagement member 376 (see FIG. 40) are the pair of polymer pads 412 which are positioned to engage the polished first and second condylar portions 32 and 34 of the femoral component 350 to inhibit any scuffing or scarring of the bearing regions. Positioned substantially orthogonal to the pads 412 are a pair of engagement fingers 420 which are sized to be nestingly received within the box 52 of the femoral component 350. Passing through the engagement member 376 is a substantially cylindrical bore 422 which slidably receives the elongated shaft 382 of the engagement shaft 372. The engagement member 376 essentially acts as an engagement and spacer block located between the femoral component 350 and the removal portion 370.

Figure 33:
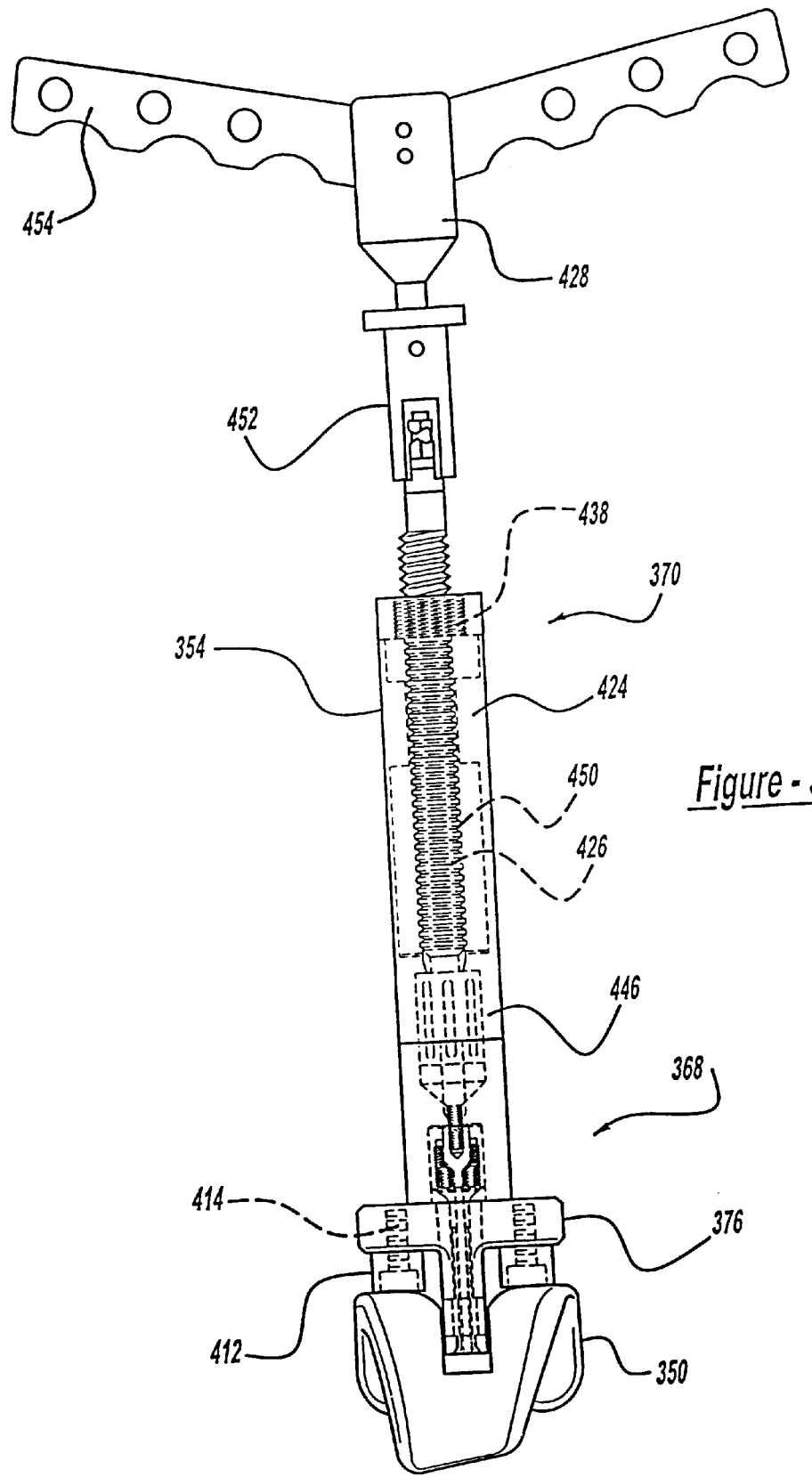
FIG. 33 is a coronal elevational view of the femoral component and seal member, along with a removal instrument in partial cross section according to the teachings of the thirteenth preferred embodiment of the present invention.
Figure 34:
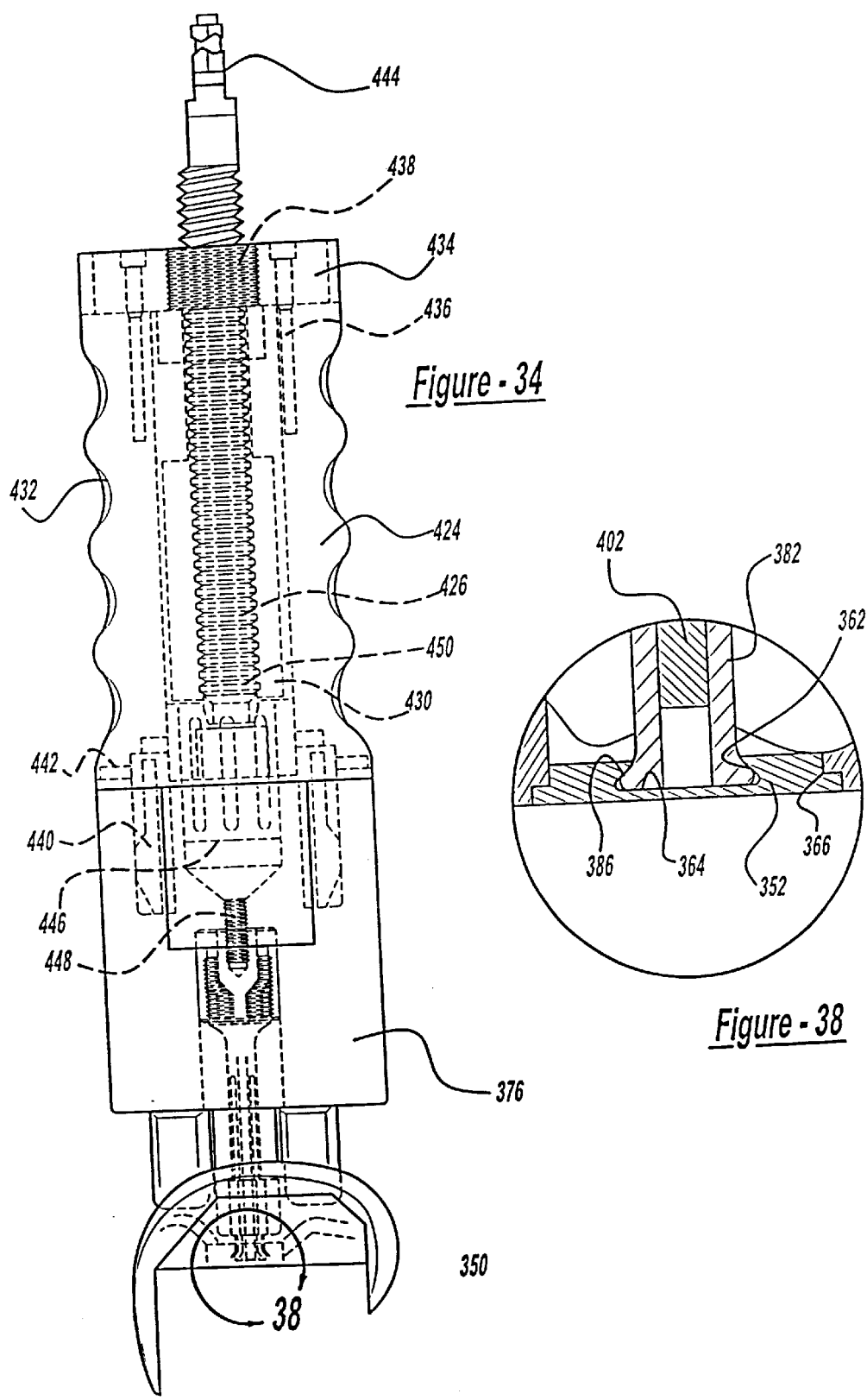
FIG. 34 is a sagittal elevational view of the femoral component and seal member, along with a removal instrument in partial cross section according to the teachings of the thirteenth preferred embodiment of the present invention.
Figure 35:
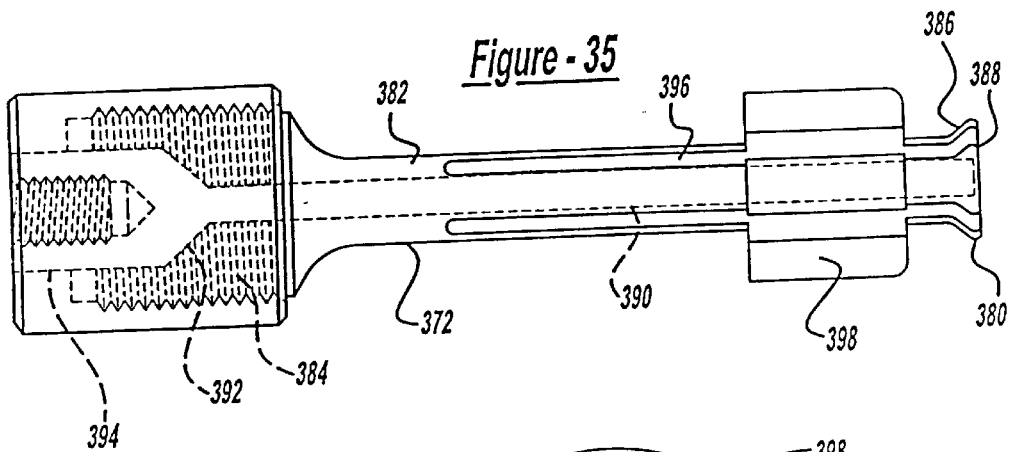
FIG. 35 is an elevational view of an assembled engagement shaft and retaining shaft according to the teachings of the thirteenth preferred embodiment of the present invention.
Figure 36:
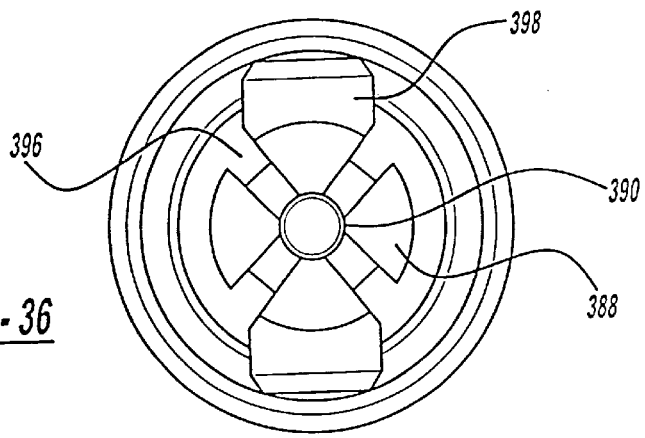
FIG. 36 is a top distal end view of the assembled engagement shaft and retaining shaft of FIG. 35.

Referring now to FIGS. 41 and 42, along with FIGS. 33 and 34, the removal portion 370 of the removal instrument 354 is shown in further detail. The removal portion 370 primarily consists of three components. These three components include a handle 424, a removal shaft 426 and a T-handle 428. The handle 424 is preferably formed from aluminum or other suitable material and defines an inner cylindrical bore 430 and includes outer opposed ribbed sidewalls 432 which are operable to be easily handled by a surgeon or user. A mating plate 434 is attached to the proximal end of the handle 424 by way of a pair of threaded screws 436. Mating plate 434 defines an internal threaded sidewall 438 which threadably engages the removal shaft 426. Positioned at the distal end of the handle 424 are a pair of engagement fingers or members 440 which are retained within the handle 424 by way of a pair of set screws 442. The fingers 444 are slidably received or nested within the opposed slots 416 of the femoral engagement component 376.

The removal shaft 426 includes an attachment or coupling portion 444 located at the proximal end of the removal shaft 426 and a rotatable chuck 446 located at the distal end of the removal shaft 426. The chuck 446 is rotatably coupled to the removal shaft 426 such that the chuck 446 may independently rotate relative to the removal shaft 426. The chuck 446 also includes a threaded nose 448 which threadably engages the threaded sidewall 406 of the retaining shaft 374. Located between the chuck 446 and the coupling portion 444 is a threaded sidewall 450 which threadably engages the inner threaded sidewall 438 of the mating plate 434. The removal shaft 426 is preferably formed from stainless steel or other appropriate sterilizable material.

The T-handle 428 includes a coupling portion 452 which nestingly receives the coupling portion 444 of the removal shaft 426. The coupling portion 452 preferably defines either an internal hexagonal, rectangular or other appropriate bore which matingly engages a similarly shaped coupling portion 444. Extending from the T-handle 428 are a pair of ribbed handle portions 454 which may be easily grasped by a surgeon or user.

Figure 43:
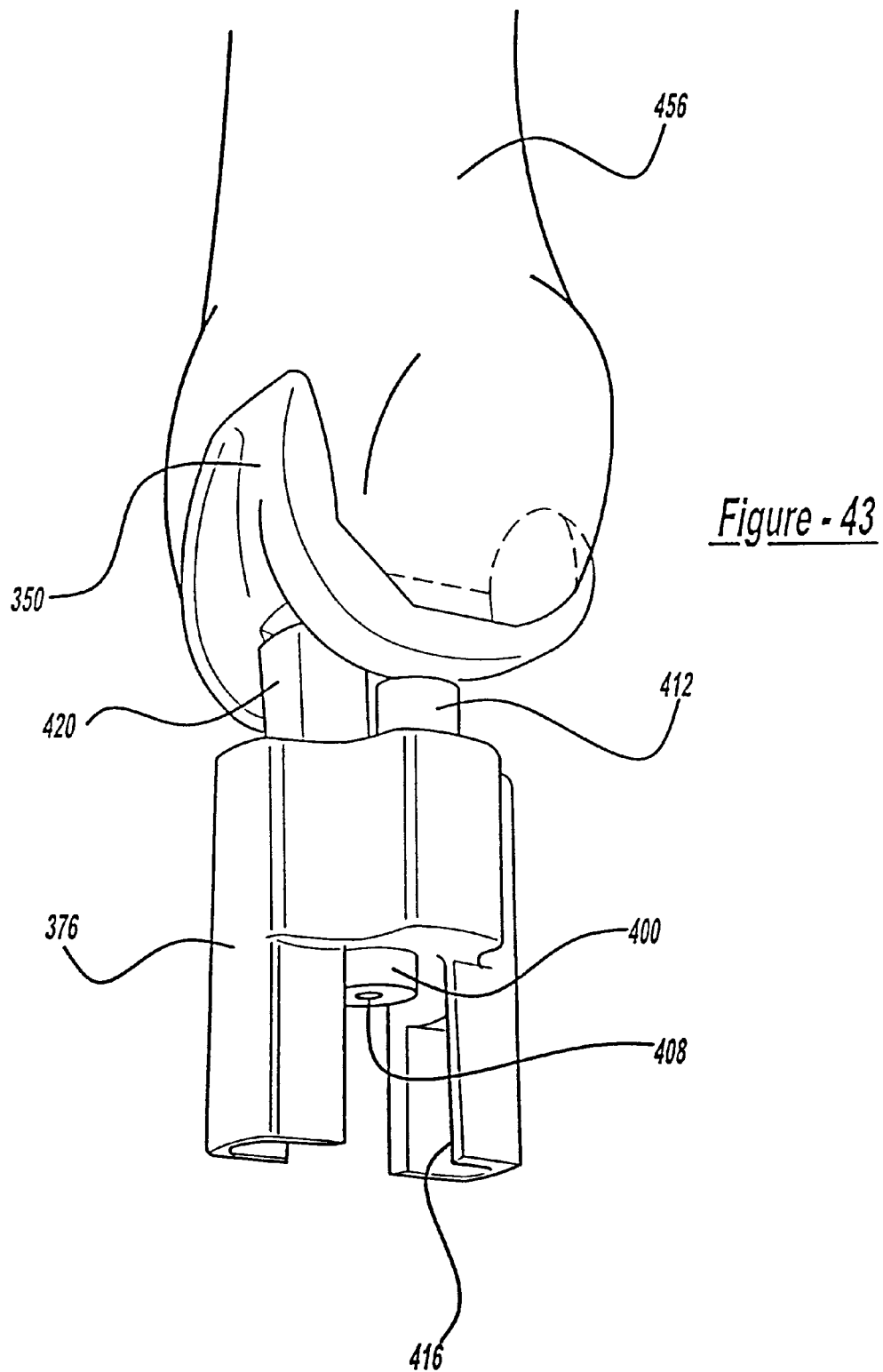
FIG. 43 is a perspective view of the femoral component and seal member shown attached to a femur (in phantom) with the engagement shaft and retaining shaft, along with the engagement member shown in engagement with the femoral component and the seal member.
Figure 44:
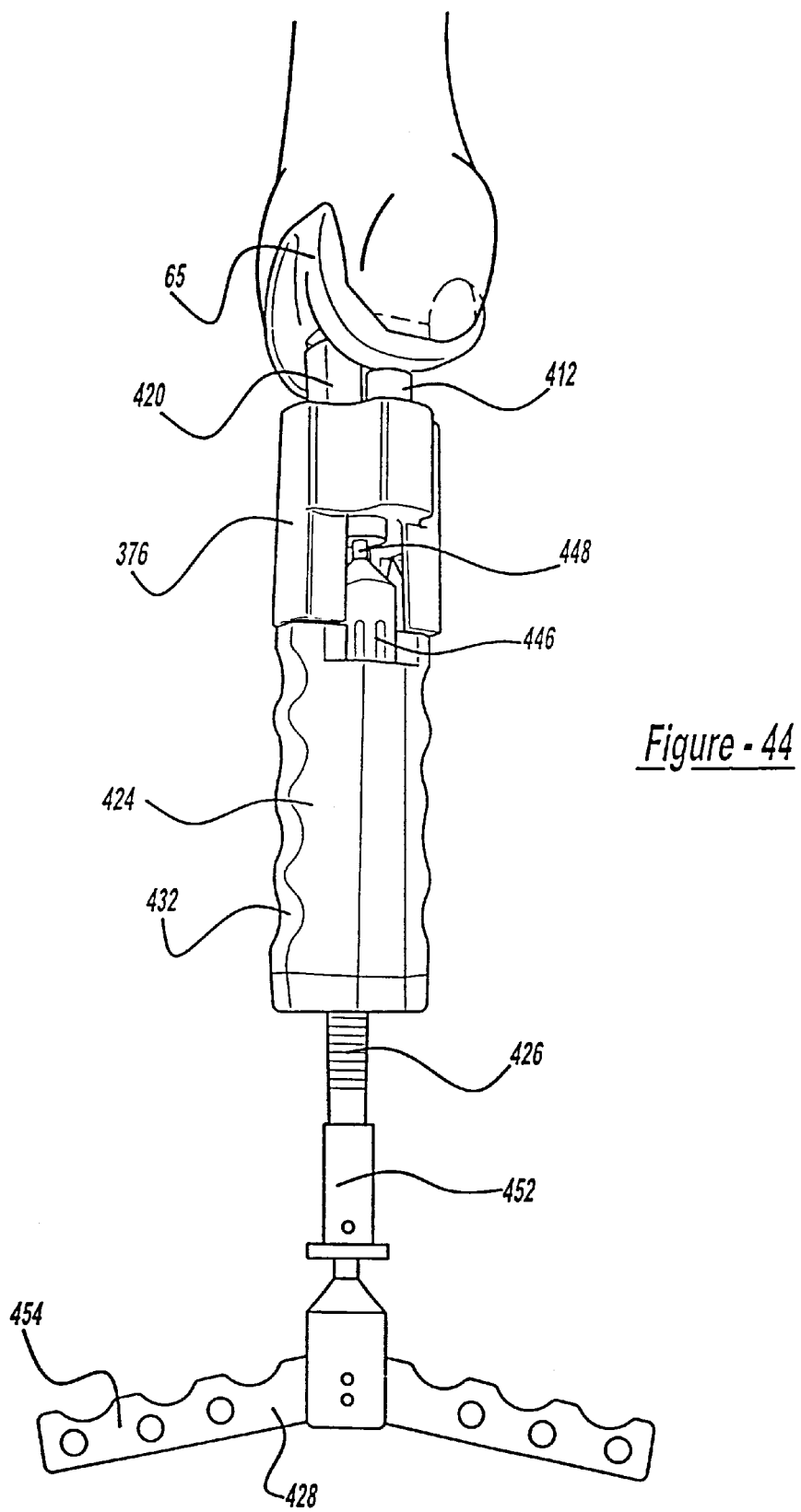
FIG. 44 is a perspective view of the removal instrument engaging the femoral component and seal member according to the teachings of the thirteenth preferred embodiment of the present invention.

Turning to FIGS. 43 and 44, the method of using the removal instrument 354 in association with the femoral component 350 is shown in further detail. The femoral component 354 is shown implanted in a femur 456 with the opening 56 sealed by the seal member 352. Should there be any necessity to obtain access to the intramedullary canal of the femur 456 after the femoral component 350 has been implanted, the seal member 352 is simply removed by way of the removal instrument 354. In this regard, the engagement portion 368 is first coupled to the femoral component 350. Specifically the distal engagement portion 380 is snappingly engaged in the recess 360 of the seal member 352. The engagement shaft 372 is also positioned within the box 52 with the guide block 398 engaging the lateral sidewalls 44 and 46 of the box 52. Once the engagement shaft 372 is engaged with the seal member 352, the retaining shaft 374 is assembled with the engagement shaft 372. In this regard, the distally extending shaft 402 is passed through the cylindrical bore 390 while the inner threaded sidewall 406 threadably engages the outer threaded sidewall 384. The distally extending shaft 402 inhibits or prevents the elongated shaft 382 from further flexing, via the channels 396, thereby preventing the tapered shoulder 386 of the distal engagement portion 380 from disengaging from the tapered sidewall 362 of the seal member 352. Once engaged, the femoral engagement member 376 is slid over the assembled engagement shaft 372 and retaining staff 378 and nested with the femoral component 350 by slidably locating engagement fingers 420 within the box 52 and engaging the polymer pads 412 relative to the first and second condylar portions 32 and 34.

With the engagement portion 368 engaging the femoral component 350, the removal portion 370 is then attached to the engagement portion 368. In this regard, the engagement fingers 440 are slidably received within the opposed channels 416 until the handle 424 abuts with the femoral engagement member 376 (see FIG. 44). The threaded nose 448 is then threadably engaged with the inner threaded sidewall 406 of the retaining shaft 374 simply by rotating the rotatable chuck 446. Once engaged, the T-handle 428 is coupled to the removal shaft 426 by way of the mating coupling portions 444 and 452. A surgeon or user will then simply rotate the T-handle 428 counterclockwise, thereby rotating the threaded sidewall 450 of the removal shaft 426 relative to the internal threaded sidewall 438 of the mating plate 434. This rotatably draws or moves the chuck 446 proximally as the handle 424 engages the femoral engagement member 376. As the chuck 446 moves proximally, the engagement shaft 372, along with the retaining shaft 374 are also moved proximally with the femoral engagement member 376 inhibiting movement of the femoral component 350.

Upon rotating the T-handle 428 sufficiently, the seal member 352 will break away from the femoral component 350 generally by deforming or fracturing the frangible lip 358 which enables access to the intramedullary canal of the femur 456 without having to remove the femoral component 350. With the seal member 352 separated from the femoral component 350, the entire removal instrument 354 becomes separated from the femoral component 350. Use of the removal instrument 354 provides for removal of the seal member 352 without substantially applying any undue or unnecessary forces on the femoral component 350 during the removal process so as to effect the securement of the femoral component 350 relative to the femur 456. In this regard, substantially all of the removal force is concentrated on the seal member 352 and not on the femoral component 350. Once the intramedullary canal of the femur 456 is exposed, an intramedullary nail or other apparatus may be passed through the femoral component 350 to correct a fracture or other deformity of the femur 456 without having to remove the femoral component 350 from the femur 456.

FIGS. 45–47 illustrate a femoral component 500 and a seal member 502 according to the teachings of a fourteenth embodiment of the present invention. Here again, like reference numerals will be used to identify like structures of the femoral component 500. The femoral component 500 includes the first condylar portion 32, the second condylar portion 34, and the inner condylar portion 40 positioned therebetween. The first and second condylar portions 32, 34 each define a bearing surface for bearing the femoral component 500 and a tibial component. The inner condylar portion 40 again defines the inner condylar recess 42 which is specifically defined by the first lateral sidewall 44 and the second lateral sidewall 46, along with the interior wall 48 and the posterior wall 50 which are each formed as a cam or lobe. These sidewalls in conjunction with an anterior wall 55, also known as an inter-bearing surface, define the perimeter of the box 52 having opening 56. Wherein, the anterior wall 55 generally defines the perimeter of the opening 56. The anterior sidewall 55 includes a radius that runs lateral to medial along its edges. Such that the edges of the anterior wall 55 defines an arc along a length of a cylinder having a center inferior of the femoral component 500. Extending into the opening 56 is a first or anterior ledge 504 and a second or posterior ledge 506. The femoral component 500 also includes the patella portion 65 which is shaped to allow anatomical tracking of a natural or prosthetic patella. Here again, the femoral component 500 is preferably formed of a unitary structure and preferably cast of a bio-compatible high strength alloy, such as cobalt chromium molybdenum alloy or other suitable material.

The seal member 502 includes a radius at its outer edges 508 and 510. A center portion 512 of the sealing member 502 is substantially flat. That is, that the outside edges 508, 510 have a radius which meets the center portion 512 which is substantially planar and non-radial across its surface. A first frangible tab 514 extends anteriorally from the center portion 508 of the sealing member 502. While a second frangible tab 516 extends posteriorly from center portion 508 of the sealing member 502. The posterior side of the sealing member 502 includes a channel 518 which has a width substantially equal to the planar section 508 and a length substantially equal to the length of the sealing member 502. A first or medial dovetail 520 extends into the channel 518 while a second or lateral dovetail 518 extends into the channel 518 as well.

The first and second tabs 514 and 516 are substantially only as wide as the center section 512. Each tab 514, 516 is generally between about 0.1 and 0.5 inches long. It will be understood, however, that any appropriate length of the tabs 514, 516 may be used. The tabs 514, 516 also have the thickness between about 0.005 and about 0.02 inches. It is understood that the thickness of the tabs 514, 516 should allow the tabs 514, 516 to be frangible or deformable. The tabs 514, 516, however, may be any appropriate thickness so that they may be deformed to remove the sealing member 502.

Sealing member 502 is affixed in the opening 56 with any appropriate means by affixing the tabs 514, 516 to the respective ledge 504, 506. Any appropriate means to affix the sealing member 502 into the opening 56 may include methods such as electron beam (e-beam) welding of the tabs 514, 516 to the ledges 504, 506. It is understood, therefore, that the sealing member 502 substantially fills the opening 56. Nevertheless, the seal member 502 generally only seals the opening 56 to debris, but not to fluids. The frangible tabs 514, 516, are formed from any appropriate material such as a cobalt chromium alloy. The entire seal member 502 may be made out the same material. Therefore, the e-beam welding adheres the tabs 514, 516 to the respective ledges 504, 506. The tabs 514, 516 may be frangible in any appropriate way such as fracturing or bending.

The removal instrument 354, described above, may also be used to remove the sealing member 502, with some modifications. Primarily, the distal engagement portion 380 would only need to be modified to include a substantially elongated shape rather than a circular shape. The channel 518 including the dovetails 520, 522 is elongated rather than circular. Therefore, the tapered shoulder 386 would simply need to be substantially equal in dimensions to the channel 518 of the sealing member 502. Once this modification is made, the process for removing the sealing member 502 from the femoral component 500, with the removal instrument 354, is substantially similar to the process described above. Briefly, once the tapered shoulder 386 and the planar distal end 388 nestingly engage the channel 518 and the dovetails 520, 522 of the removal instrument 354 may be operated to remove the sealing member 502. After the distal engagement portion is snappingly engaged into the channel 518, the distally extending shaft 402 inhibits or prevents the elongated shaft 382 from flexing, thus not allowing it to disengage from the channel 518.

Also as discussed above, after the removal instrument 354 has been attached to the sealing member 502, it may be operated such that the seal member 502 will break away from the femoral component 500 by deforming or fracturing the tabs 514, 516. Removal of the seal member 502 enables access to the intermedullary canal of the femur (not particularly illustrated) without requiring the removal of the femoral component 500. With the seal member 502 separated from the femoral component 500, the entire removal instrument 354 becomes separated from the femoral component 500. Use of the removal instrument 354 provides for removal of the seal member 502 without substantially applying undue or unnecessary forces to the femoral component 500 during the removal process, so as to not effect the securement of the femoral component 500 relative to the femur. Therefore, substantially all of the removal forces are concentrated on the seal member 502 rather than the femoral component 500. Once the seal member 502 has been removed, any apparatus necessary may be inserted into the intermedullary canal of the femur.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A knee joint prosthesis that provides access to an intramedullary canal of a femur after the knee joint prosthesis has been implanted, the knee prosthesis comprising:
    a femoral component having at least a first bearing surface spaced apart from a second bearing surface;
    an inter-bearing surface extending between said first bearing surface and said second bearing surface defining a bore passing through said inter-bearing surface;
    a ledge extending from said inter-bearing surface into said bore;
    a seal member operable to substantially fill said bore in said femoral component; and
    a frangible tab extending from said seal member operable to engage said ledge;
    wherein said seal member may be substantially removed after said femoral component is implanted to enable access to the intramedullary canal of the femur without requiring removal of the knee joint prosthesis from the femur.

2. The knee joint prosthesis of claim 1 wherein said seal member defines a recess within said seal member which is operable to be engaged by a removal instrument.

3. The knee joint prosthesis of claim 2 wherein said removal instrument includes an engagement portion operable to engage said femoral component and a removal portion operable to remove said seal member from said femoral component.

4. The knee joint prosthesis of claim 3 wherein said engagement portion includes an engagement shaft operable to engage said recess in said seal member and an engagement member operable to engage a first condylar portion and a second condylar portion of said femoral component.

5. The knee joint prosthesis as defined in claim 4 wherein said engagement member further engages an inner condylar portion extending between said first condylar portion and said second condylar portion.

6. The knee joint prosthesis of claim 1 wherein said first bearing surface is formed from a first condylar portion and said second bearing surface is formed from a second condylar portion and said bore passes through said inter bearing surface extending between said first condylar portion and said second condylar portion.

7. The knee joint prosthesis of claim 1 wherein said frangible tab of said seal member is welded to said ledge of said femoral component.

8. The knee joint prosthesis of claim 1 wherein said seal member includes a first radius edge, a second radius edge, and a planar portion extending between said first radius edge and said second radius edge.

9. The knee joint prosthesis of claim 8 wherein said frangible tab extends from said planar portion operable to interconnect said seal member and said femoral component.

10. A knee joint prosthesis system for enabling access to an intramedullary canal of a femur, the knee joint prosthesis system comprising:
    a femoral component having at least a first bearing surface defining an opening passing through said femoral component;
    a tibial component having a portion adapted to engage said first bearing surface;
    a seal member operable to substantially fill said opening, wherein said seal member defines an elongated recess;
    a tab extending from said seal member to operably interconnect said seal member and said femoral component; and
    a removal instrument operable to engage said elongated recess of said seal member to substantially remove said seal member from said femoral component to enable access to the intramedullary canal of the femur.

11. The knee joint prosthesis system as defined in claim 10 wherein said tabs are removably affixed to said femoral component by way of electron beam welding.

12. The knee joint prosthesis system as defined in claim 10 wherein said removal instrument includes an engagement portion and a removal portion, said engagement portion operable to engage said seal member and said removal portion operable to substantially remove said seal member from said femoral component.

13. The knee joint prosthesis system as defined in claim 12 wherein said engagement portion includes an engagement shaft operable to engage said seal member and an engagement member operable to engage said femoral component wherein said removal portion concentrates its removal force on said seal member without substantially applying a removal force on said femoral component.

14. The knee joint prosthesis system as defined in claim 13 wherein said femoral component includes a first condylar portion having a first femoral bearing surface, a second condylar portion having a second femoral bearing surface, and an inner condylar portion extending between said first condylar portion and said second condylar portion which defines said opening and said engagement member of said removal instrument having a pair of engagement pads operable to engage said first and second condylar portions and further having a pair of guide fingers operable to be inserted within said inner condylar portion of said femoral component.

15. The knee joint prosthesis system as defined in claim 10 wherein said seal member includes a first radius edge and a second radius edge wherein said elongated recess is disposed between said first radius edge and said second radius edge.

16. The knee joint prosthesis system as defined in claim 15 wherein said tab extends from said seal member adjacent said elongated recess, wherein said tab includes a frangible tab which is operable to be deformed upon said removal instrument removing said seal member from said femoral component.

17. The knee joint prosthesis system as defined in claim 10 further comprising a tibial component having a second bearing surface operable to articulate with said first bearing surface of said femoral component.

18. A method for enabling access to an intramedullary canal of a femur through a femoral knee joint prosthesis, said method comprising:

providing the femoral knee joint prosthesis including an opening therethrough;

removably affixing a seal member by affixing a tab, extending from said seal member, to a ledge extending into said opening of said femoral knee joint prosthesis; wherein said seal member substantially fills said opening passing through the femoral knee joint prosthesis;

implanting said femoral knee prosthesis including said seal member;

providing a removal instrument operable to engage the seal member; and substantially removing the seal member from the femoral knee joint prosthesis upon engaging the seal member with the removal instrument after the femoral knee joint prosthesis has been implanted to enable access to the intramedullary canal of the femur without removing the femoral knee joint prosthesis from the femur.

19. The method as defined in claim 18 further comprising engaging a channel in the seal member with the removal instrument, wherein said channel recess is substantially collinear with said seal member.

20. The method as defined in claim 19 further comprising engaging the femoral component with an engagement member to concentrate the removal force on the seal member.

21. The method as defined in claim 20 further comprising rotating a removal shaft to remove the seal member from the femoral knee joint prosthesis without removing the femoral knee joint prosthesis from the femur.

* * * * *